US011787123B2

(12) United States Patent
McLaren et al.

(10) Patent No.: US 11,787,123 B2
(45) Date of Patent: *Oct. 17, 2023

(54) HIGH FREQUENCY WELDING FOR HEADGEAR

(71) Applicant: Fisher & Paykel Healthcare Limited, Auckland (NZ)

(72) Inventors: Mark Arvind McLaren, Auckland (NZ); Andrew James Webb, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 128 days.

This patent is subject to a terminal disclaimer.

(21) Appl. No.: 17/177,625

(22) Filed: Feb. 17, 2021

(65) Prior Publication Data

US 2021/0170694 A1    Jun. 10, 2021

Related U.S. Application Data

(63) Continuation of application No. 15/518,728, filed as application No. PCT/IB2015/057812 on Oct. 13, 2015, now Pat. No. 10,926,478.

(Continued)

(51) Int. Cl.
*B29C 65/02* (2006.01)
*A61M 16/06* (2006.01)
(Continued)

(52) U.S. Cl.
CPC ......... *B29C 65/02* (2013.01); *A61M 16/0683* (2013.01); *B23K 13/04* (2013.01);
(Continued)

(58) Field of Classification Search
CPC .... B65B 13/325; B23K 15/0046; B23K 11/10
See application file for complete search history.

(56) References Cited

U.S. PATENT DOCUMENTS 4,090,897 A    5/1978  Minick
4,311,540 A *  1/1982  Hill ...................... B29C 66/034
                                              156/580.2

(Continued)

FOREIGN PATENT DOCUMENTS

JP       H02-16034        1/1990
WO    WO 2010/066004     6/2010
WO    WO 2015/043119     4/2015

OTHER PUBLICATIONS

Australian Government, IP Australia, Examination Report No. 2 for Standard Patent Application, Application No. 2015332097, dated Jan. 20, 2021, in 4 pages.

(Continued)

*Primary Examiner* — Matthew J Daniels
*Assistant Examiner* — Wayne K. Swier
(74) *Attorney, Agent, or Firm* — Knobbe Martens Olson & Bear LLP

(57) ABSTRACT

Welded headgear sections can be produced by using a weld tool having pins protruding from a weld region contact surface to deliver high-frequency electromagnetic energy to a weld region defined by overlapping top and bottom headgear straps. The pins fully penetrate the top strap and at least partially penetrate the bottom strap. The pins concentrate the electromagnetic energy to achieve a weld joint of acceptable weld strength and aesthetic appeal.

19 Claims, 21 Drawing Sheets

Related U.S. Application Data

(60) Provisional application No. 62/063,303, filed on Oct. 13, 2014.

(51) Int. Cl.
  *B23K 13/04* (2006.01)
  *B29C 65/00* (2006.01)
  *B23K 103/00* (2006.01)
  *B29L 31/00* (2006.01)

(52) U.S. Cl.
  CPC ..... *B29C 66/7254* (2013.01); *A61M 2207/00* (2013.01); *A61M 2207/10* (2013.01); *B23K 2103/30* (2018.08); *B29L 2031/753* (2013.01)

(56) References Cited

U.S. PATENT DOCUMENTS

| | | | |
|---|---|---|---|
| 4,767,492 A * | 8/1988 | Fukusima | B29C 66/7373 53/DIG. 2 |
| 4,795,511 A | 1/1989 | Wouters et al. | |
| 5,468,335 A * | 11/1995 | Mainolfi | B29C 66/81433 156/580.2 |
| 5,545,275 A | 8/1996 | Herrin et al. | |
| 6,009,925 A | 1/2000 | Hall et al. | |
| 6,648,206 B2 | 11/2003 | Nelson et al. | |
| 7,793,815 B2 | 9/2010 | Shimizu et al. | |
| 8,651,163 B1 | 2/2014 | Widhalm | |
| 10,079,380 B2 | 9/2018 | Oh et al. | |
| 2003/0205565 A1* | 11/2003 | Nelson | B29C 66/73921 219/148 |
| 2008/0210360 A1 | 9/2008 | Soccard | |
| 2011/0248069 A1 | 10/2011 | Khakhalev et al. | |
| 2014/0190486 A1 | 7/2014 | Dunn et al. | |
| 2015/0090405 A1 | 4/2015 | Hull et al. | |
| 2017/0225387 A1 | 8/2017 | McLaren et al. | |
| 2018/0126657 A1 | 5/2018 | Yasuda et al. | |

OTHER PUBLICATIONS

International Search Report, PCT/IB2015/057812, dated Jan. 13, 2016 in 3 pages.
Examination Report for Australian Patent Application No. 2015332097; dated May 13, 2020; 4 pages.

* cited by examiner

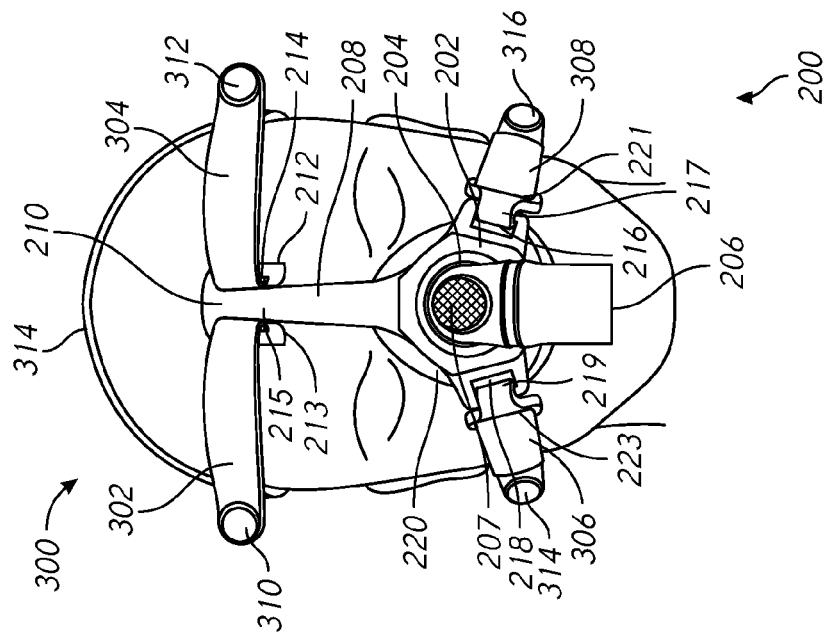
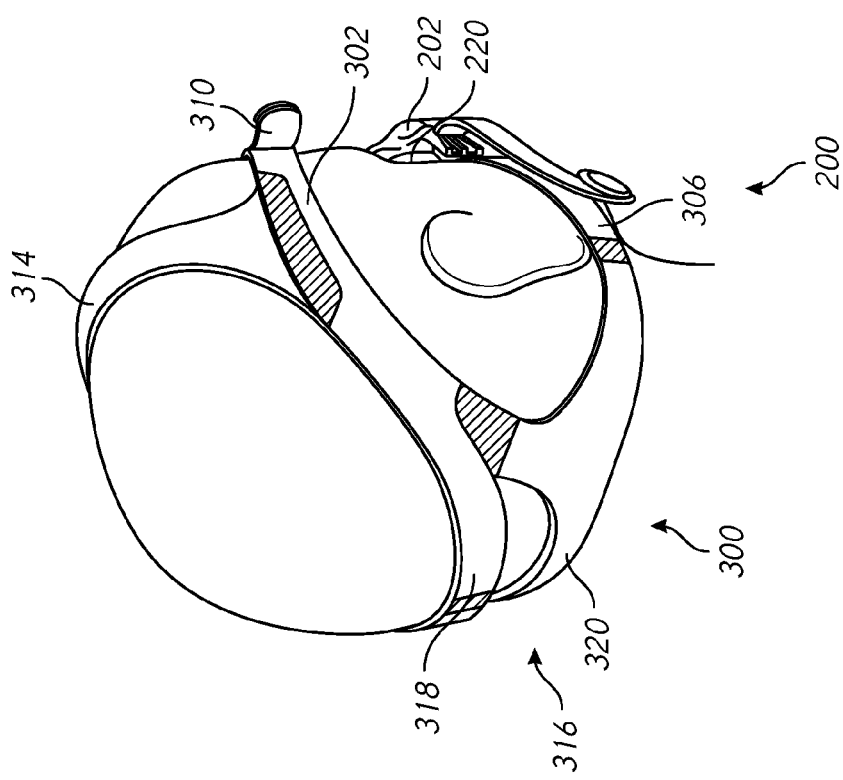
FIG. 2A
FIG. 2B

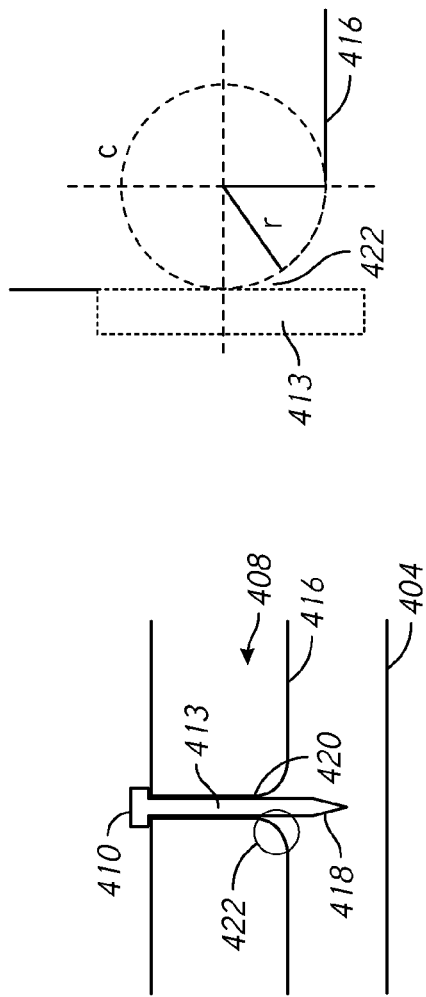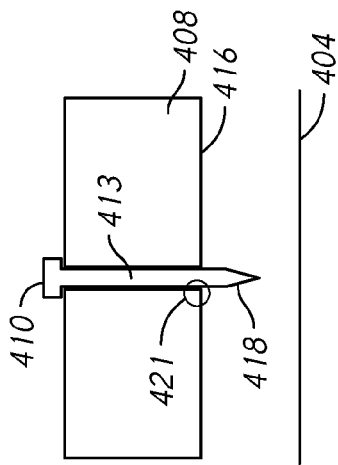
FIG. 9B
FIG. 9A
FIG. 10

HIGH FREQUENCY WELDING FOR HEADGEAR

INCORPORATION BY REFERENCE OF PRIORITY APPLICATIONS

The entireties of any and all priority applications are hereby incorporated by reference herein and made a part of the present disclosure.

BACKGROUND

Technical Field

The present disclosure generally relates to headgear for patient interfaces.

Description of the Related Art

In patients suffering from obstructive sleep apnea (OSA), muscles that normally keep the upper airway open relax during slumber to the extent that the airway is constrained or completely closed off, a phenomenon often manifesting itself in the form of snoring. When this occurs for a period of time, the patient's brain typically recognizes a threat of hypoxia and partially wakes the patient in order to open the airway so that normal breathing may resume. The patient may be unaware of these waking episodes, which may occur as many as several hundred times per session of sleep. This partial awakening may significantly reduce the quality of the patient's sleep, over time potentially leading to a variety of symptoms, including excessive daytime sleepiness, chronic fatigue, elevated heart rate, elevated blood pressure, weight gain, headaches, irritability, depression and anxiety.

Obstructive sleep apnea is commonly treated with the application of positive airway pressure (PAP) therapy. PAP therapy involves delivering a flow of gas to a patient at a therapeutic pressure above atmospheric pressure that will reduce the frequency and/or duration of apneas, hypopneas, and/or flow limitations. The therapy is often implemented by using a positive airway pressure device to deliver a pressurized stream of air through a conduit to a patient through a patient interface or mask positioned on the face of the patient.

SUMMARY

A patient interface for use with PAP therapy or other respiratory therapies involving the administration of gas can comprise headgear that helps to retain the patient interface on the face of a patient. The headgear generally interfaces with a frame that serves as a channel through which gas is delivered to the patient and the headgear comprises one or more straps that pass around the patient's head. To reduce the material waste and cost of producing headgear, instead of producing the entire headgear from a single blank of material, it is desirable to cut headgear straps from the material and join them via stitching, adhesives, or welding processes, e.g., high-frequency welding processes. In high-frequency welding, the straps can be overlapped to define an overlap weld region. The straps can be forced together (e.g., placed under pressure) through the use of a weld tool adapted to deliver high-frequency energy to the weld region. High-frequency welding is useful for joining straps quickly and in a sterile manner. However, in some cases, the welded joints can have visible markings, burns or bulges that reduce the aesthetic appeal and/or comfort of the headgear.

Certain features, aspects and advantages of at least one of the configurations disclosed herein include the realization that overlapping headgear straps or other materials can be joined through the use of a weld tool adapted to deliver high-frequency energy, wherein the weld tool comprises pins extending from a contact surface of the weld tool that at least partially penetrate each of the overlapping headgear straps. To diffuse the heat and/or energy generated at the contact surface of the weld tool near the pins, portions of the surface of the weld tool surrounding the pins can be inwardly chamfered. The contact surface of the weld tool can have beveled or rounded edges to further reduce the undesired concentration of energy along parts of the surfaces of headgear straps. One or both of the headgear straps can be specially formed to reduce potential distortions in shape encountered in the welding process. More aesthetically pleasing and/or comfortable headgear may thus be formed.

Thus, in accordance with certain features, aspects and advantages of at least one of the embodiments disclosed herein, a method of producing headgear for a patient interface is disclosed. The method comprises using a weld tool to apply high-frequency energy to a weld region defined by overlapping top and bottom straps. The weld tool comprises pins that at least partially penetrate both the top and bottom straps. In some configurations, the pins may extend from a contact surface of the weld tool. In some configurations, the material comprised in at least one of the straps may be at least in part polar or may comprise polar molecules, moieties or sections.

In some configurations, the top and bottom headgear straps are positioned on a weld base and the weld tool is forced against the weld region to apply pressure to the headgear straps.

In some configurations, the pins fully penetrate the top headgear strap and partially penetrate the bottom headgear strap. In some such configurations, the pins penetrate 20% or about 20% of the depth of the bottom headgear strap. In other configurations, the pins penetrate 1% to 99% or about 1% to about 99% of the depth of the bottom headgear strap, or about 10% to about 90%, or about 20% to about 80%, or about 30% to about 70%, or about 40% to about 60%, or about 50% of the depth of the bottom headgear strap.

In some configurations, the surface of the weld tool that faces the weld region (e.g., the contact surface of the weld tool) comprises beveled or rounded edges.

In some configurations, portions of the surface of the weld tool surrounding the pins are inwardly chamfered. In some such configurations, the chamfered portions are substantially arcuate or rounded. In some such configurations, the substantially arcuate chamfered portions are defined by crater-like recesses present in the surface of the weld tool. In some such configurations, the curvatures of the sides of the crater-like recesses are defined by substantially circular cross-sections of the weld tool having radii x that are proportional to the average distance between pins y according to the range of ratios x:y=0.3 to 0.4 or about 0.3 to about 0.4.

In some configurations, the pins are arranged in a plurality of rows. In some such configurations, the rows are offset such that pins are present in a honeycomb arrangement.

In some configurations, the pins are arranged such that each pin is substantially equidistant from adjacent pins.

In some configurations, either of top or bottom headgear straps comprises an edge section and a body section, the edge section having a smaller width than the body section. In some such configurations, the width of the edge section is in the range of 80% to 90% or about 80% to about 90% of the width of the body section. A substantially curved transition region can lie between the body section and the edge section.

In some configurations, the average distance between adjacent pins is in the range of about 1.5 mm to about 2.0 mm.

In some configurations, the average distance between adjacent pins is in the range of about 3 to about 4 times the average width of the pins.

Additionally, in accordance with certain features, aspects and advantages of at least one of the embodiments disclosed herein, a method of welding two straps of material together is disclosed. The method comprises using a weld tool to apply high-frequency energy to a weld region defined by overlapping top and bottom straps. The weld tool comprises pins that fully penetrate the top strap and penetrate 20% or about 20% of the depth of the bottom strap. In other configurations, the pins penetrate 1%-99% or about 1%-about 99% of the depth of the bottom strap, or about 10% to about 90%, or about 20% to about 80%, or about 30% to about 70%, or about 40% to about 60%, or about 50% of the depth of the bottom strap. The material comprised in at least one of the straps is at least in part polar or comprises polar molecules, moieties or sections.

In some configurations, the top and bottom straps are positioned on a weld base and the weld tool is forced against the weld region to apply pressure to the straps.

In some configurations, the surface of the weld tool that faces the weld region (e.g., the contact surface of the weld tool) comprises beveled or rounded edges.

In some configurations, portions of the surface of the weld tool surrounding the pins are inwardly chamfered. In some such configurations, the chamfered portions are substantially arcuate. In some such configurations, the substantially arcuate chamfered portions are defined by crater-like recesses present in the surface of the weld tool. In some such configurations, the curvatures of the sides of the crater-like recesses are defined by substantially circular cross-sections of the weld tool having radii x that are proportional to the average distance between pins y according to the range of ratios x:y=0.3 to 0.4 or about 0.3 to about 0.4.

In some configurations, the pins are arranged in a plurality of rows. In some such configurations, the rows are offset such that the pins are present in a honeycomb arrangement.

In some configurations, the pins are arranged such that each pin is substantially equidistant from adjacent pins.

In some configurations, either the top or bottom straps comprises an edge section and a body section, the edge section having a smaller width than the body section. In some such configurations, the width of the edge section is in the range of 80% to 90% or about 80% to about 90% of the width of the body section. A substantially curved transition region can lie between the body section and the edge section.

In some configurations, the average distance between adjacent pins is in the range of 1.5 mm to 2.0 mm or about 1.5 mm to about 2.0 mm.

In some configurations, the average distance between adjacent pins is in the range of 3 to 4 or about 3 to about 4 times the average width of the pins.

Additionally, in accordance with certain features, aspects and advantages of at least one of the embodiments disclosed herein, a method of welding two straps of material together is disclosed. The method comprises using a weld tool to apply high-frequency energy to a weld region defined by overlapping top and bottom straps, wherein either the top or bottom straps comprises an edge section and a body section, the edge section having a smaller width than the body section. The material comprised in at least one of the straps is at least in part polar or comprises polar molecules, moieties or sections.

In some configurations, the weld tool comprises pins that at least partially penetrate both the top and bottom straps. In some such configurations, pins fully penetrate the top strap and partially penetrate the bottom strap. The pins can be arranged in a plurality of rows. In some such configurations, the rows are offset such that the pins are present in a honeycomb arrangement. The pins can be arranged such that each pin is substantially equidistant from adjacent pins.

In some configurations, portions of the surface of the weld tool surrounding the pins are inwardly chamfered. In some such configurations, the chamfered portions are substantially arcuate. In some such configurations, the substantially arcuate chamfered portions are defined by crater-like recesses present in the surface of the weld tool. In some such configurations, the curvatures of the sides of the crater-like recesses are defined by substantially circular cross-sections of the weld tool having radii x that are proportional to the average distance between pins y according to the ratio x:y=about 0.3 to about 0.4.

In some configurations, the top and bottom straps are positioned on a weld base and the weld tool is forced against the weld region to apply pressure to the straps.

In some configurations, the surface of the weld tool that faces the weld region (e.g., the contact surface of the weld tool) comprises beveled or rounded edges.

Additionally, in accordance with certain features, aspects and advantages of at least one of the embodiments disclosed herein, a method of welding two straps of material together is disclosed. The method comprises using a weld tool to apply high-frequency energy to a weld region defined by overlapping top and bottom straps, the weld tool comprising pins that at least partially penetrate both the top and bottom straps, wherein the portions of the surface of the weld tool surrounding the pins are inwardly chamfered. The material is at least in part polar or comprises polar molecules.

In some configurations, the chamfered portions are substantially arcuate. In some such configurations, the substantially arcuate chamfered portions are defined by crater-like recesses present in the surface of the weld tool. In some such configurations, the curvatures of the sides of the crater-like recesses are defined by substantially circular cross-sections of the weld tool having radii x that are proportional to the average distance between pins y according to the ratio x:y=about 0.3 to about 0.4.

Additionally, in accordance with certain features, aspects and advantages of at least one of the embodiments disclosed herein, a method of welding two straps of material together is disclosed. The method comprises forcing a weld tool against a weld region defined by overlapping top and bottom straps positioned on a weld base and applying high-frequency energy using the weld tool, the weld tool comprising pins that at least partially penetrate both the top and bottom straps, wherein a surface of the weld tool that contacts the weld region comprises beveled or rounded edges.

Additionally, in accordance with certain features, aspects and advantages of at least one of the embodiments disclosed herein, headgear is disclosed. The headgear is produced at least in part using one or more of the methods described above or elsewhere in this disclosure.

Additionally, in accordance with certain features, aspects and advantages of at least one of the embodiments disclosed herein, a patient interface is disclosed. The patient interface comprises headgear produced at least in part using one or more of the methods described above or elsewhere in this disclosure. In some configurations, the patient interface further comprises a cushion module adapted to be positioned over the face of a patient and a frame removably secured to the cushion module, the frame adapted to receive a gases flow from a flow generator.

Additionally, in accordance with certain features, aspects and advantages of at least one of the embodiments disclosed herein, a respiratory therapy system is disclosed. The respiratory therapy system comprises a flow generator (e.g. PAP device), a patient interface and a conduit extending between the flow generator and the patient interface. In some configurations, the respiratory therapy system also comprises a humidifier in-line between the flow generator and the patient interface. The patient interface comprises headgear produced at least in part using one or more of the methods described above or elsewhere in this disclosure.

Additionally, in accordance with certain features, aspects and advantages of at least one of the embodiments disclosed herein, a weld tool is disclosed. The weld tool is adapted to be used in a high-frequency welding process. The weld tool comprises a plurality of pins extending from a contact surface of the weld tool, wherein portions of the contact surface surrounding the pins are inwardly chamfered.

In some configurations, the chamfered portions are substantially arcuate. In some such configurations, the substantially arcuate chamfered portions are defined by crater-like recesses present in the surface of the weld tool. In some such configurations, the curvatures of the sides of the crater-like recesses are defined by substantially circular cross-sections of the weld tool having radii x that are proportional to the average distance between pins y according to the ratio x:y=about 0.3 to about 0.4.

In some configurations, the pins are arranged in a plurality of rows. In some configurations, the rows are offset such that the pins are present in a honeycomb arrangement. The pins can be arranged such that each pin is substantially equidistant from adjacent pins.

Additionally, in accordance with certain features, aspects and advantages of at least one of the embodiments disclosed herein, a weld tool is disclosed. The weld tool is adapted to be used in a high-frequency welding process. The weld tool comprises a plurality of pins extending from a contact surface of the weld tool. The contact surface comprises beveled or rounded edges.

In some configurations, the pins are arranged in a plurality of rows. In some such configurations, the rows are offset such that the pins are present in a honeycomb arrangement. The pins can be arranged such that each pin is substantially equidistant from adjacent pins.

Additionally, in accordance with certain features, aspects and advantages of at least one of the embodiments disclosed herein, a welding system is disclosed. The welding system comprises a weld tool adapted to the used in a high-frequency welding process. The weld tool comprises a plurality of pins extending from a contact surface of the weld tool. At least portions of the contact surface of the weld tool surrounding the pins are inwardly chamfered. The welding system additionally comprises a weld base. The weld base is adapted to support material to be welded. In use, the weld tool is forced against the material supported by the base.

In some configurations, the welding system additionally comprises a stop adapted to limit the range of axial motion between the weld tool and the weld base. In some such configurations, the stop extends outwardly from the weld tool and rests upon a raised portion of the weld base.

In some configurations, the chamfered portions are substantially arcuate. In some configurations, the substantially arcuate chamfered portions are defined by crater-like recesses present in the surface of the weld tool. In some such configurations, the curvatures of the sides of the crater-like recesses are defined by substantially circular cross-sections of the weld tool having radii x that are proportional to the average distance between pins y according to the ratio x:y=about 0.3 to about 0.4.

In some configurations, the pins are arranged in a plurality of rows. In some such configurations, the rows are offset such that the pins are present in a honeycomb arrangement. The pins can be arranged such that each pin is substantially equidistant from adjacent pins.

Additionally, in accordance with certain features, aspects and advantages of at least one of the embodiments disclosed herein, a welding system is disclosed. The welding system comprises a weld tool adapted to be used in a high-frequency welding process. The weld tool comprises a plurality of pins extending from a contact surface of the weld tool. The contact surface comprises beveled or rounded edges. The welding system additionally comprises a weld base. The weld base is adapted to support material to be welded. In use, the weld tool is forced against the material supported by the base.

In some configurations, the welding system further comprises a stop adapted to limit the range of axial motion between the weld tool and the weld base. In some such configurations, the stop extends outwardly from the weld tool and rests upon a raised portion of the weld base.

Additionally, in accordance with certain features, aspects and advantages of at least one of the embodiments disclosed herein, a welding system for welding together top and bottom sheets of fabric is disclosed. The welding system comprises a weld tool adapted to be used in a high-frequency welding process. The weld tool comprises a plurality of pins extending from a contact surface of the weld tool. The welding system additionally comprises a weld base. The weld base has a cavity to support the top and bottom sheets in an overlapping relationship. The weld tool and the cavity have a corresponding shape such that the weld tool engages the cavity and the contact surface applies pressure to the top and bottom sheets.

In some configurations, the pins are arranged in a single-file row along an outer edge of the weld tool.

In some configurations, the pins are arranged in a double-file row along an outer edge of the weld tool.

In some configurations, the pins are arranged in a staggered row along an outer edge of the weld tool.

In some configurations, the pins have a diameter within a range of 0.3 mm to 1.0 mm.

In some configurations, centers of the pins are spaced apart a distance of 2.5 mm to 6.0 mm.

In some configurations, the weld tool is formed from a thermally insulating material.

In some configurations, the contact surface of the weld tool has a thermally insulating coating.

In some configurations, the pins are arranged in a plurality of rows. In some such configurations, the rows are offset such that the pins are present in a honeycomb arrangement. The pins can be arranged such that each pin is substantially equidistant from adjacent pins.

In some configurations, the pins in the honeycomb arrangement are arranged in a hexagonal shape around a center pin.

In some configurations, the pins arranged in the hexagonal shape are enclosed within a hexagonal-shaped area that surrounds the pins. Outer segments that define the hexagonal-shaped area are tangent to outer edges of outermost adjacent pins. A pin density ratio is defined as a ratio between a total area of the pins versus an area of the hexagonal-shaped area.

In some configurations, the pin density ratio is equal to 33.85%.

In some configurations, each pin has a diameter of 0.5 mm, and wherein a distance between each pin is 1.0 mm.

In some configurations, the pins in the honeycomb arrangement are arranged in concentric hexagons around a center pin.

In some configurations, the pins arranged in concentric hexagons are enclosed within a hexagonal-shaped area that surrounds the pins. Outer segments that define the hexagonal-shaped area are tangent to outer edges of outermost adjacent pins. A pin density ratio is defined as a ratio between a total area of the pins versus an area of the hexagonal-shaped area.

In some configurations, the pin density ratio is equal to 28.37%.

In some configurations, each pin has a diameter of 0.5 mm and a distance between each pin is 1.0 mm. The honeycomb arrangement can have two concentric hexagons, and a radial distance between centers of adjacent pins is 1.0 mm.

In some configurations, the pins are arranged in a concentric circular arrangement having pins arranged in at least one concentric circle around a center pin.

In some configurations, the pins arranged in at least one concentric circle are enclosed within a circular-shaped area that surrounds the pins. An outermost circle that defines the circular area is defined by radially outermost points of the outermost pins. A pin density ratio is defined as a ratio between a total area of the pins versus an area of the circular-shaped area.

In some configurations, the pin density ratio is equal to 18.34%.

In some configurations, each pin has a diameter of 0.5 mm. The concentric circular arrangement includes three concentric circles, and a radial distance between centers of adjacent pins is 1.0 mm.

In some configurations, the pins are arranged in a square grid arrangement having each row squarely aligned with an adjacent row and each row having a quantity of pins that is equal to a quantity of rows.

In some configurations, the pins are arranged such that each pin is spaced equidistant to an adjacent pin.

In some configurations, an orthogonal distance between an outer edge of each pin is equal a diameter of each pin. The pins arranged in the square grid arrangement are enclosed within a square-shaped area that surrounds the pins. Outer segments that define the square-shaped area are tangent to outer edges of outermost adjacent pins. A pin density ratio is defined as a ratio between a total area of the pins versus an area of the square-shaped area.

In some configurations, the pin density ratio is equal to 21.71%.

In some configurations, the diameter of each pin is equal to 0.5 mm.

In some configurations, the pins have either a first diameter or a second diameter, and the pins alternate between the first diameter and the second diameter along a length of each row.

In some configurations, the pins arranged in the square grid arrangement are enclosed within a square-shaped area that surrounds the pins. Outer segments that define the square-shaped area are tangent to outer edges of outermost alternating pins. A pin density ratio is defined as a ratio between a total area of the pins versus an area of the square-shaped area.

In some configurations, the pin density ratio is equal to 13.59%

In some configurations, the first diameter is equal to 0.5 mm and the second diameter is equal to 0.25 mm. An orthogonal distance between an outer edge of each pin is equal 0.625 mm.

In some configurations, the pins are arranged such that each pin is spaced equidistant to an adjacent pin along a length of the row.

In some configurations, the pins are enclosed within a square-shaped area that surrounds the pins. Outer segments that define the square-shaped area are tangent to outer edges of outermost pins. A pin density ratio is defined as a ratio between a total area of the pins versus an area of the square-shaped area.

In some configurations, the pin density ratio is equal to 19.63%.

In some configurations, the diameter of each pin is equal to 0.5 mm and a distance between centers of pins of adjacent rows in a direction perpendicular to a length of the row is 1.0 mm.

In some configurations, the pins have identical diameters along a length of the row and the pins in each row alternate between a first diameter and a second diameter.

In some configurations, the pins are enclosed within a square-shaped area that surrounds the pins. Outer segments that define the square-shaped area are tangent to outer edges of outermost pins. A pin density ratio is defined as a ratio between a total area of the pins versus an area of the square-shaped area.

In some configurations, the pin density ratio is equal to 14.09%.

In some configurations, the first diameter is equal to 0.5 mm and the second diameter is equal to 0.25 mm. A distance between centers of adjacent pins along a length of the row is equal to 1.0 mm, and a distance between centers of pins of adjacent rows in a direction perpendicular to a length of the row is 1.0 mm.

In some configurations, the pin densities are within a range of 10-50%.

In some configurations, the pin densities are within a range of 15-35%.

In some configurations, the pin densities are within a range of 15-25%.

In some configurations, the pins have a pointed tip.

BRIEF DESCRIPTION OF THE DRAWINGS

Specific embodiments and modifications thereof will become apparent to those skilled in the art from the detailed description herein having reference to the figures that follow, of which:

FIGS. 2A and 2B show rear perspective and front views, respectively, of a patient wearing a patient interface.

FIGS. 9A and 9B show a cross-section of a diagram of a high-frequency welding system and a close-up view of the cross-section of the diagram, respectively.

FIG. 10 shows a cross-section of a diagram of a high-frequency welding system.

DETAILED DESCRIPTION

Figure 1:
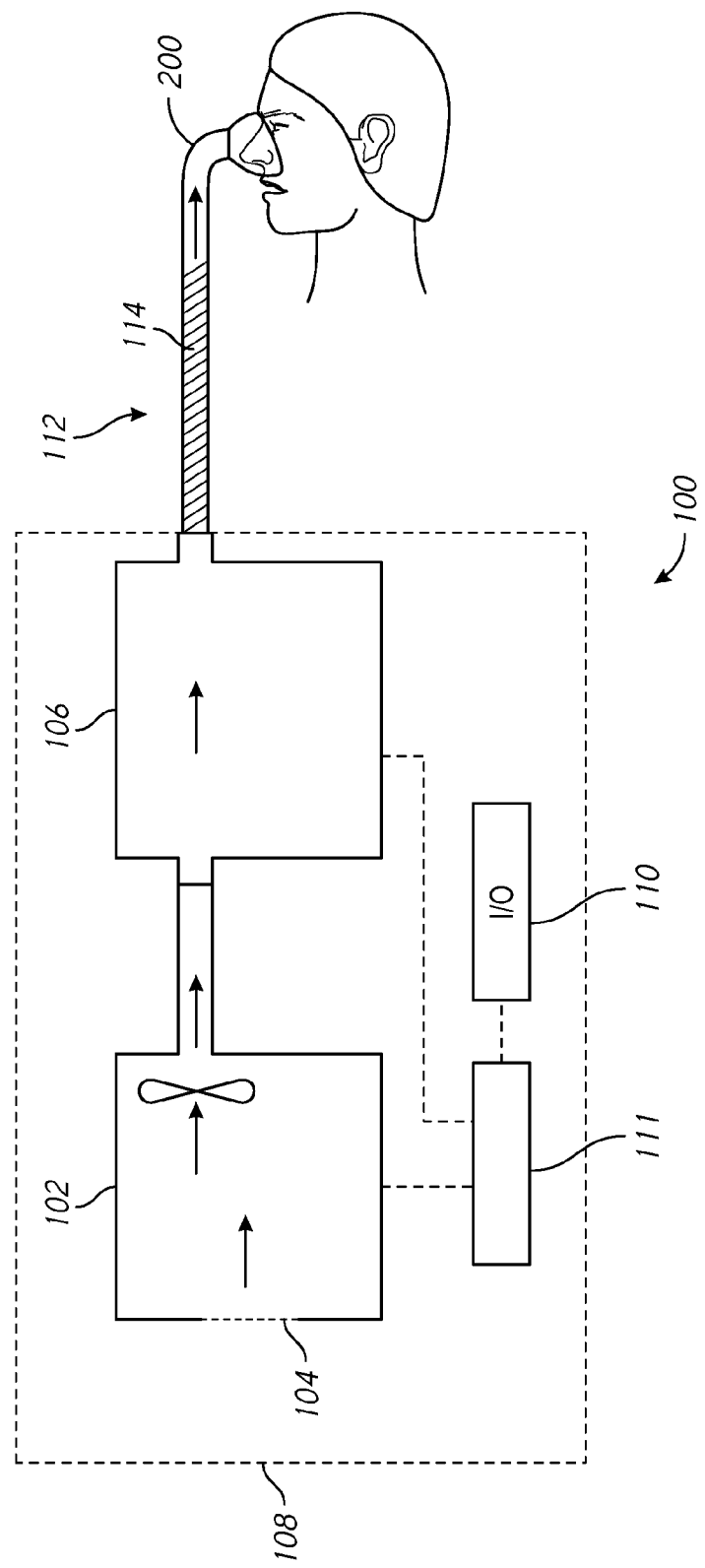
FIG. 1 shows a schematic diagram of a respiratory therapy system.

With reference to the non-limiting exemplary embodiment illustrated in FIG. 1, a respiratory therapy system 100 is shown. The respiratory therapy system 100 comprises a flow generator 102. The flow generator 102 comprises a PAP device. The flow generator 102 receives gases from a gases inlet 104 and propels them to a humidifier 106. The flow generator 102 and the humidifier 106 may be part of an integrated flow delivery system or may share a housing 108. The humidifier 106 heats and humidifies the gases. Heated and humidified gases are passed from a humidifier outlet to a gases conduit 112. The gases conduit 112 comprises a heater 114. The heater 114 reduces or prevents the condensation of moisture along the walls of the gases conduit 112. Gases are passed from the gases conduit 112 to a patient interface 200 through which they are delivered to a patient. The respiratory therapy system 100 comprises a controller 111 that controls the operation of the flow generator 102. The controller 111 also controls the operation of the humidifier 106. The respiratory therapy system 100 comprises an input/output (I/O) module 110. The I/O module 110 comprises a way for a user to interact with and set parameters for the flow generator 102 and/or humidifier 106 as well as receive information regarding the operation of the respiratory therapy system 100 and/or its components. The I/O module 110 may comprise, for example, buttons, knobs, dials, switches, levers, touch screens, speakers, displays and/or other input or output elements. In some configurations, the humidifier 106 may not be present. In some configurations, the gas conduit 112 may not have a heater 114. In some configurations, the flow generator 102 may comprise elements other than PAP devices, including but not limited to high flow therapy devices or ventilation devices.

FIGS. 2A and 2B demonstrate a non-limiting patient interface 200 that can be used with the respiratory therapy system 100 shown in FIG. 1. As illustrated, the patient interface 200 comprises a nasal mask. In some configurations, the patient interface 200 may comprise a sealing or non-sealing interface. For example, the patient interface 200 may comprise an oral mask, an oro-nasal mask, a full face mask, a nasal pillows mask, an endotracheal tube, a combination of the above, or some other gas conveying system or apparatus.

The patient interface 200 shown comprises a frame 202 adapted to receive gases from a gases source (for example, the flow generator 102 described elsewhere in this disclosure with reference to FIG. 1) and channel them to the patient. An aperture 204 in the frame 202 is adapted to receive an elbow component 206 configured to interface with a gases delivery conduit (for example, the gases conduit 112 described elsewhere in this disclosure with reference to FIG. 1). The elbow component 206 may be adapted to swivel or rotate (through, for example, a ball-joint connection). The elbow component 206 comprises vent holes 207 that permit a leak flow to escape the patient interface 200. The vent holes 207 can help to mitigate the build-up of carbon dioxide in the patient interface 200 and/or gas delivery conduit. The frame 202 interfaces with a cushion module 220. The cushion module 220 comprises a relatively rigid or hard cushion housing adapted to interface with the frame 202 and a relatively flexible or soft cushion adapted to sealingly engage with the patient's face to provide a substantially sealed gas passageway between the patient and the gases delivery conduit. The frame 202 comprises a neck 208 that substantially extends along the head of the patient across, for example, the nasalis muscles and the procerus muscles. The neck 208 ends in a forehead support 210 comprising first and second hooked legs 212, 213. Openings 214, 215 are defined between the hooked legs 212, 213 and the forehead support 210. The frame 202 also comprises apertures 216, 218.

Headgear 300 interfaces with the frame 202 to provide a way for retaining the patient interface 200 on the face. A four-point connection with the frame 202 is made available using the openings 214, 215 present near the forehead support 210 and using the apertures 216, 218 present on the frame 202. The headgear 300 comprises left and right top straps 304, 302 and left and right bottom straps 308, 306. The top and bottom straps 302, 304, 306, 308 join at a back section 316. The back section 316 comprises a top back strap 318 and a bottom back strap 320. The headgear 300 additionally comprises a crown strap 314 that extends between the left and right top straps 304, 302. To interface with the frame 202, the left and right bottom straps 308, 306 are looped through openings 223, 221 present in hook connectors 217, 219 that are retained in the apertures 216, 218 present on the frame 202. The left and right bottom straps 308, 306 comprise loop patches 316, 314 that allow the straps 308, 306 to be loosened or tightened and fixed into place (for example, using corresponding hooked regions on the straps 308, 306 to facilitate a hook-and-loop fastening arrangement) after they are looped through the openings 223, 221. The left and right top straps 304, 302 are looped at the ends. The looped ends are placed over the hooked legs 212, 213 such that they are retained between the forehead support 210 and the hooked legs 212, 213. Similarly, the left and right top straps 304, 302 comprise loop patches 312, 310 that allow straps 304, 302 to be loosened or tightened and fixed into place (for example, using corresponding hooked regions on the straps 304, 302 to facilitate a hook-and-loop fastening arrangement) after they are positioned on the hooked legs 212, 213.

Figure 3:
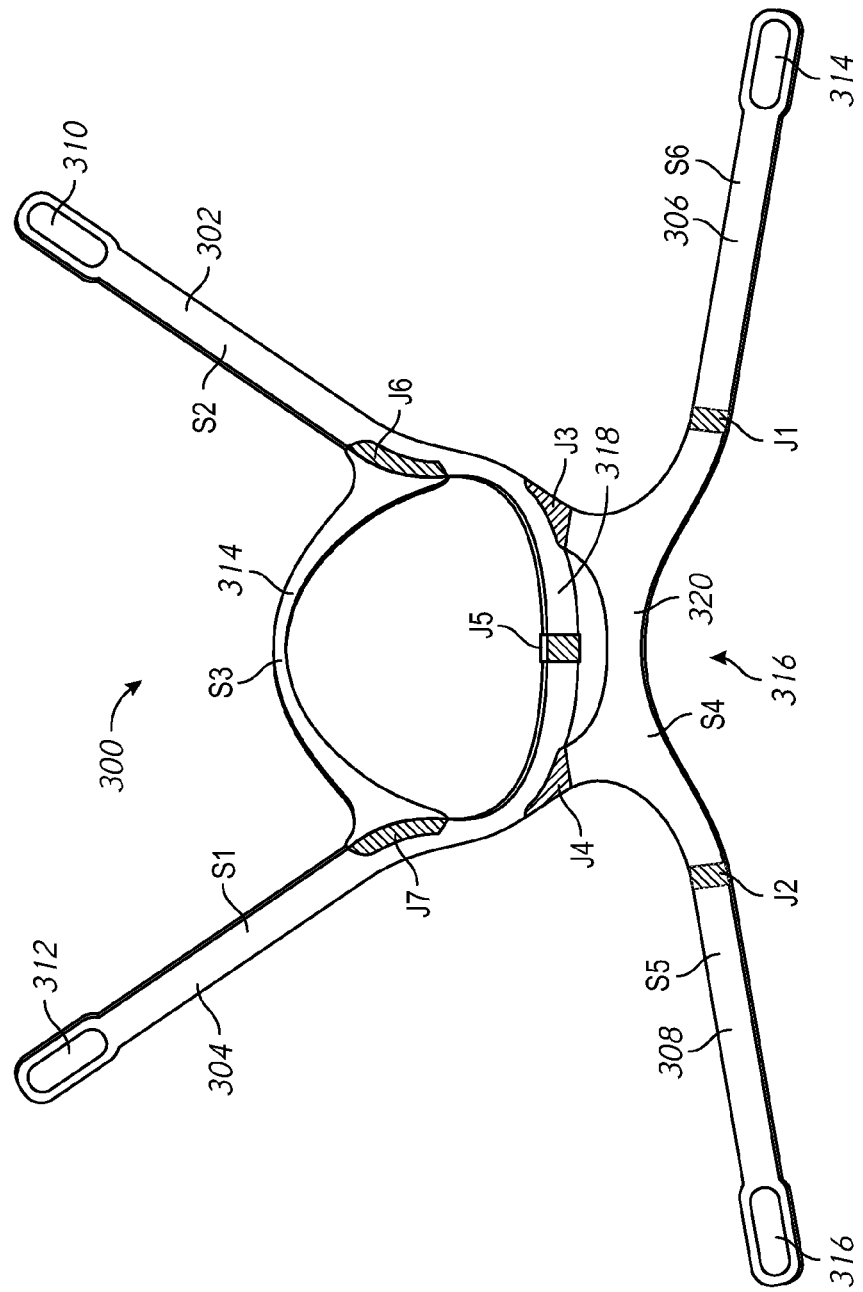
FIG. 3 shows a view of respiratory headgear that is shown in FIGS. 2A and 2B.

FIG. 3 shows another view of the headgear 300 illustrated in FIGS. 2A and 2B. As shown, the headgear 300 comprises a plurality of strap sections S joined at joints J. In particular, the left and right top straps 304, 302 form strap sections S1, S2 and are joined at J5 to form the top back strap 318 of the back section 316. The left and right top straps 304, 302 are also joined at joints J7, J6 via the crown strap 314, which forms strap section S3. The bottom back strap 320, which forms strap section S4 is joined to the top back strap 318 through joints J4, J3, and interfaces with left and right bottom straps 308, 306 (sections S5, S6) through joints J2, J1. In the illustrated configuration, the joints J are formed through the use of high-frequency welding. The strap sections S can be formed from any material appropriate for use with respiratory headgear, including but not limited to fabrics, fabric/foam composites or Breath-O-Prene™.

Figure 4:
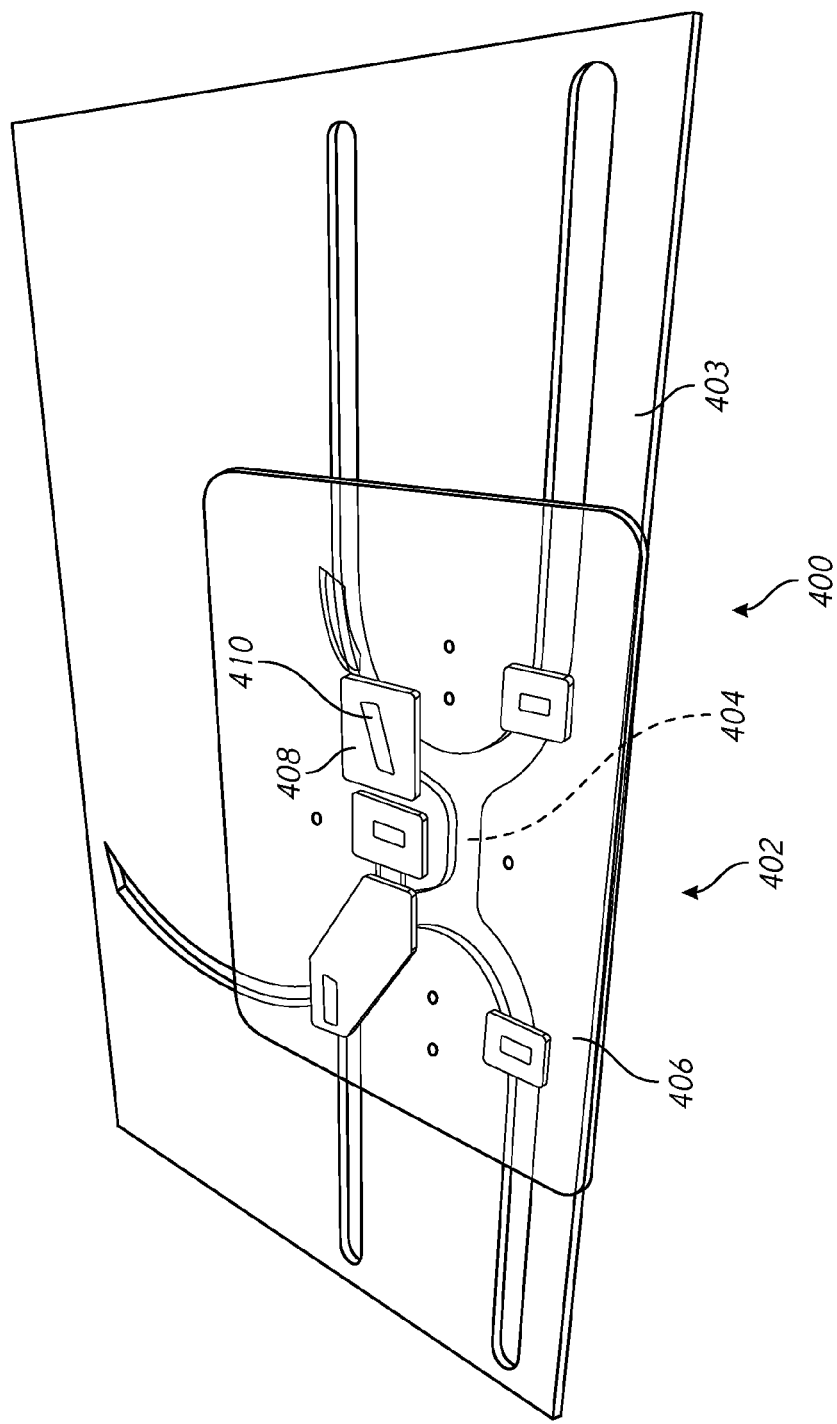
FIG. 4 shows a high-frequency welding system.

FIG. 4 illustrates a high-frequency welding system 400 adapted to manufacture headgear from sections (e.g. strap sections) S of headgear (for example, but not limited to, the headgear described elsewhere in this disclosure with reference to FIG. 3). High-frequency welding as described in this disclosure refers to a method of joining sections of material (e.g., straps, sheets, films, etc.) (the material comprised in at least one of the sections at least in part being polar or comprising polar molecules, moieties or sections) together using a rapidly alternating electric field (including, but not necessarily limited to, electric fields having alternation frequencies in the range of 13 to 100 or about 13 to about 100 megahertz, or, for example, 27.12 or about 27.12 megahertz). The welding system 400 comprises a weld base (e.g., anvil) 402 comprising a relatively elevated section 403 and a relatively depressed section 404 adapted to hold overlapping straps of headgear. A stop plate 406 rests on the relatively elevated section 403 of the weld base 402. The stop plate 406 comprises apertures through which weld tools (e.g. horn) 408 protrude. In use, the weld tools 408 may be energized with electromagnetic energy (using an energy source, not shown), causing the weld tools 408 to generate alternating electric fields that cause polar molecules in the straps of material to oscillate and orient themselves with respect to the field. This movement of the polar molecules generates heat, causing a temperature increase that results in the melting of the sheets. The weld tools 408 are forced (using a press, not shown) against weld regions defined by overlapping top and bottom sheets to apply pressure to the sheets. It should be understood that 'top' and 'bottom' as used in this disclosure can be interpreted as referring to positioning with respect to a weld tool 408 rather than with respect to gravity. The top sheet can refer to the sheet closest to the weld tool 408 and the bottom sheet can refer to the sheet furthest from the weld tool 408. The combination of melting and pressure promotes the formation of a welded joint between the sheets. The weld tools 408 further comprise rows of pin heads 410 that are further described below with reference to the accompanying figures. Although the weld tools 408 shown are rectangular or hexagonal, it should be understood that the weld tools 408 could have other shapes, including, but not limited to, triangular or circular shapes. In some configurations, the stop plate 406 could be integrally formed with or be in the form of a single piece with one or more of the weld tools 408.

Figure 5:
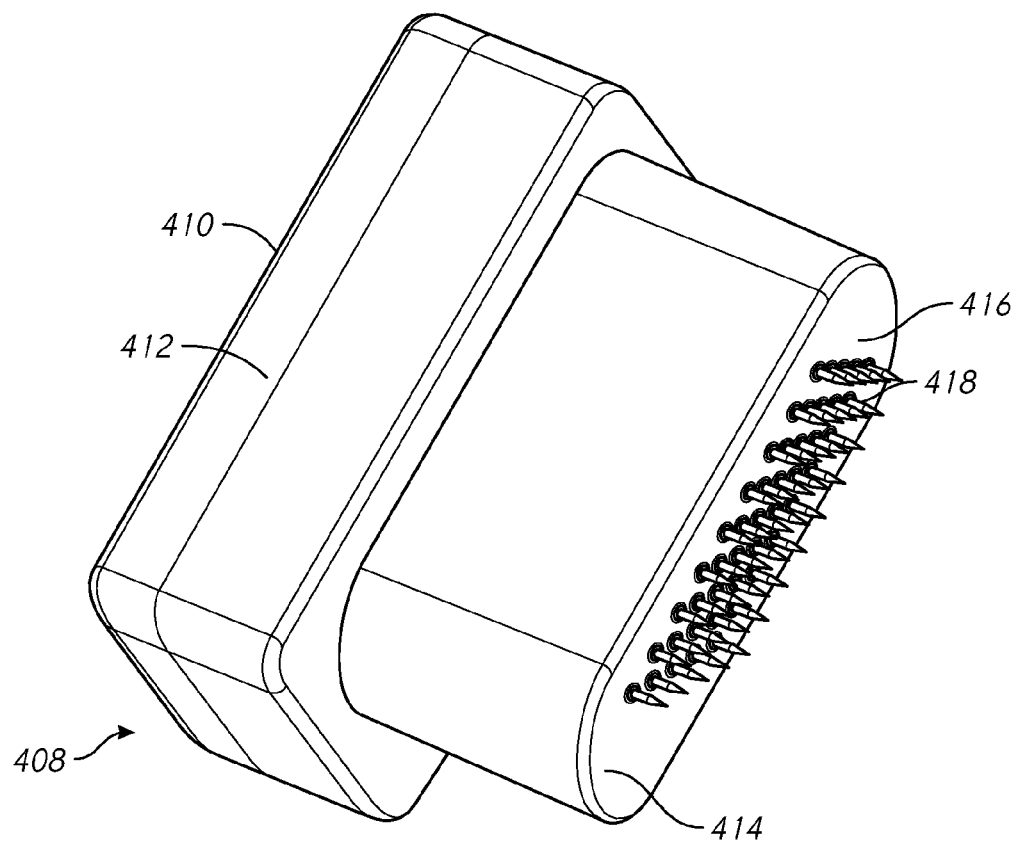
FIG. 5 shows a weld tool for use in high-frequency welding.

FIG. 5 illustrates a weld tool 408 configured to be used with the high frequency welding system 400. The weld tool 408 comprises a top section 412 that rests on the stop plate 406 (see FIG. 4) in use and cooperates with the stop plate 406 to limit the range of axial motion between the weld tool 408 and the weld base 402. The weld tool 408 comprises a bottom section 414. The bottom section 414 comprises a lower average cross-sectional area than the cross-sectional area of the top section 412. The bottom section 414 is adapted to protrude through apertures in the stop plate 406 as described elsewhere in this disclosure with reference to FIG. 4. The bottom section 414 comprises a contact surface 416 that is forced against straps of material to apply pressure. The weld tool 408 comprises a plurality of pins 413 (see also FIGS. 7A-7D and the accompanying disclosure), the pins comprising pin heads 410 and ends 418. The pins 413 enter the weld tool 408 through apertures in the top section 412, extend through the body of the weld tool 408 and protrude (e.g., via ends 418) through the bottom section 414. In alternative configurations, the weld tool 408 could comprise only a single pin. In some configurations, the pins 413 could be permanently positioned in the weld tool 408 (for example, via the use of adhesives or frictional fits or couplings). In some configurations, and particularly if the weld tool 408 is integrally formed with the stop plate 406, the weld tool may only comprise a single section. Usage of the weld tool 408 is further described below with reference to the accompanying figures.

Figure 6A:
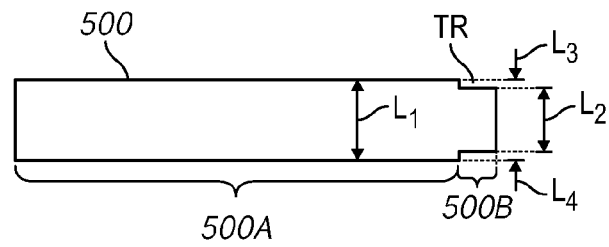
FIGS. 6A-6D show a top-down diagram detailing the positioning of various components during a high-frequency welding process.
Figure 6B:
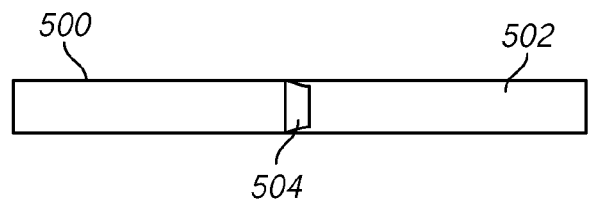

FIGS. 6A-6D show non-limiting exemplary diagrams for the positioning of various components during a high-frequency welding method. The illustrated straps are headgear straps. However, straps of materials for forming other articles (including, but not limited to, articles of clothing) could be used. FIG. 6A shows a bottom strap 500. As used above or elsewhere in this disclosure, it should be understood that the words 'top' and 'bottom' do not refer to the relative positions of the straps with respect to the force of gravity but, instead, refer to the relative positions of the straps with respect to the weld tool 408. The bottom strap 500 comprises a body section 500A of a first width and an edge section 500B of a second width. The edge section 500B is inwardly stepped relative to the body region 500A. In other words, the edge section 500B is of a smaller width than the body section 500A. In the illustrated configuration, the body section 500A has a width $L_1$ of 17 mm or about 17 mm. The edge section 500B has a width $L_2$ of 15 mm or about 15 mm with insteps $L_3$, $L_4$ of 1 mm on either side of the edge section 500B. In some configurations, the width of the edge section 500B may be in the range of about 60% to about 97% of the width of the body section 500A, or about 65% to about 95%, or about 70% to about 93%, or about 80% to about 90% of the width of the body section 500A. Maintaining the desired width of the body section 500A relative to the width of the edge section 500B helps to mitigate the tendency of molten material to flow too far outwardly from the weld region 504 (see FIG. 6B), which can cause undesired bulging at the sides of the finished weld joint formed at the weld region 504. If two rectangular straps are welded together, a weld joint with bulging edges along the sides of the joint is more likely to be formed. Using a strap with inset portions can create cavities in which excess molten material can reside. A substantially curved transition region TR lies between the body section 500A and the edge section 500B. The transition region TR promotes adequate distribution of energy during welding, allowing for the formation of an aesthetically acceptable weld joint. In alternative configurations, the transition region TR may not be present. In FIG. 6B, a portion of a substantially rectangular top strap 502 is laid over the bottom strap 500. A weld region 504 is defined by the overlapping top and bottom straps 502, 504. However, in other configurations, both of the straps 502, 500 could have substantially rectangular shapes. In still other configurations, either or both of the straps could have other shapes, including, but not limited to, circular or triangular shapes.

Figure 6C:
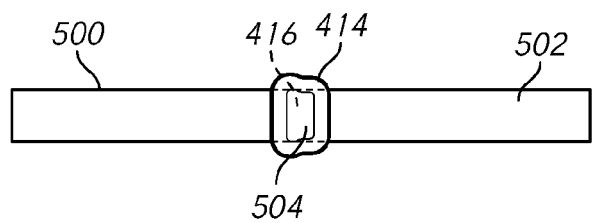
Figure 6D:
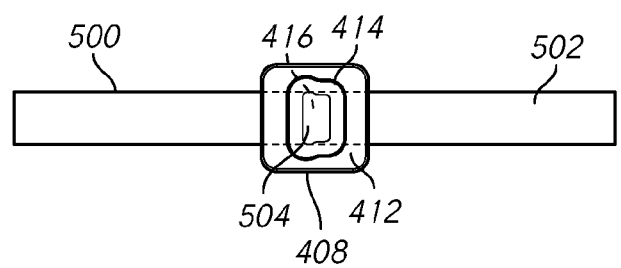

FIG. 6C shows the position of the bottom section 414 of the weld tool 408 over the weld region 504. As shown, at least the contact surface 416 of the bottom section 414 (i.e., on the underside of the bottom section 414) comprises a stepped shape similar to shape of the bottom strap 500. Using a contact surface 416 with a stepped shape promotes the distribution of energy along the contact surface 416, further mitigating undesired bulging at the sides of the weld joint formed at the weld region 504. However, in other configurations the contact surface 416 could have other shapes, including, but not limited to, rectangular, circular or triangular shapes. Additionally, as shown, the bottom section 414 extends outwardly past the weld region 504 and/or contact surface 416. In some configurations, the edges of the bottom section 414 may extend, for example, 1 mm or about 1 mm past the edges of the weld region 504. The larger footprint of the bottom section 414 helps to improve the tolerance of errors in proper placement of the weld tool 408. FIG. 6D shows the position of the top section 412. As shown, the top section 412 is substantially rectangular with rounded edges. However, in other configurations, the top section 412 may have other shapes, including, but not limited to, triangular or circular shapes.

FIGS. 7A-7D illustrate a non-limiting exemplary high-frequency welding method. FIG. 7A demonstrates again a weld region 504 defined by overlapping top and bottom straps 502, 500. The straps 502, 500 can lie in the depressed section 404 of the base plate 402. As described elsewhere in this disclosure, the weld tool 408 comprises a top section 412 and a bottom section 414 comprising a contact surface 416. The weld tool 408 comprises pins 413 that pass through the weld tool 408, extending from pin heads 410 positioned on the top section 412 to ends 418 projecting from the contact surface 416 of the bottom section 414. The top section 412 can cooperate with the stop plate 406 and the elevated section 403 of the weld base 402 to limit axial movement of the weld tool 408 relative to the weld base 402 (see FIG. 7B). As the weld tool 408 is moved into the weld region 504, the contact surface 416 is forced against the weld region 504. The urging of the contact surface 416 against the weld region 504 provides pressure to the straps 502, 500. The ends 418 of the pins 413 that project outwardly from the contact surface 416 penetrate the entire depth of the top strap 502 and partially penetrate the bottom strap 500.

In the illustrated configuration, the stop plate 406 and the elevated portion 403 of the weld base 402 are positioned such that a clearance $L_2$ of 2.5 mm or about 2.5 mm is present between the contact surface 416 and the recessed portion 404 of the weld base 402. The ends 418 of the pins 413 project a length $L_3$ of about 1.5 mm from the contact surface 416. About 1 mm of clearance $L_1$ is present between the ends 418 of the pins 413 and the recessed portion 404. The ratio $L_2:L_1$ in the illustrated configuration, then, is about 2.5:1. In other configurations, the ratio $L_2:L_1$ can comprise other values. For example, the ratio $L_2:L_1$ can be in the range of 2:1 to 3:1 or about 2:1 to about 3:1. In other configurations, the straps 502, 500 are each 1.25 mm or about 1.25 mm thick when compressed by the weld tool 408. The ends 418, then, penetrate the full 1.25 mm thickness of the top strap 502 and 0.25 mm or about 0.25 mm of the depth of the bottom strap 500. In other words, the pins 413 penetrate 20% or about 20% of the depth of the bottom strap 500. In other configurations, the pins 413 can penetrate about 5% to about 50% of the depth of the bottom strap 500, or about 10% to about 40%, or about 15% to about 30%. In still other configurations, the pins 413 can penetrate 1% to 99% or about 1% to about 99% of the depth of the bottom strap 500, or about 10% to about 90%, or about 20% to about 80%, or about 30% to about 70%, or about 40% to about 60%, or about 50% of the depth of the bottom strap 500.

It has been discovered that the depth of penetration of the bottom strap 500 can factor into the weld strength and aesthetic appeal of the weld joint formed at the weld region 504. If the penetration depth is too high, in some cases the ends 418 may not deliver enough energy to the interface between the top and bottom straps 502, 500. Additionally, too much energy may be delivered to the bottom strap 500, which can promote excessive melting or burning of the bottom strap 500. If the penetration depth is too low, in some cases the ends 418 may not project far enough into the bottom strap 500, or the ends 418 may not project at all into the bottom strap 500. Too much energy may be delivered to the top strap 502, which can promote excessive melting or burning of the top strap 502.

Additionally, it has been discovered that it is desirable to minimize the clearance $L_1$ to decrease the chance of electrical arcing from the contact surface 416 and/or ends 418 to the weld base 404. Undesired electrical arcing can cause excessive melting and/or burns in one or both of the straps 502, 500, which can lead to aesthetically unappealing welded joints. In some configurations, the clearance $L_1$ can be about 80% of the pin length $L_3$ (ratio $L_1:L_3$=about 0.8). In other configurations, the ratio $L_1:L_3$ can be in the range of, for example, about 0.7 to about 0.9.

Figure 7A:
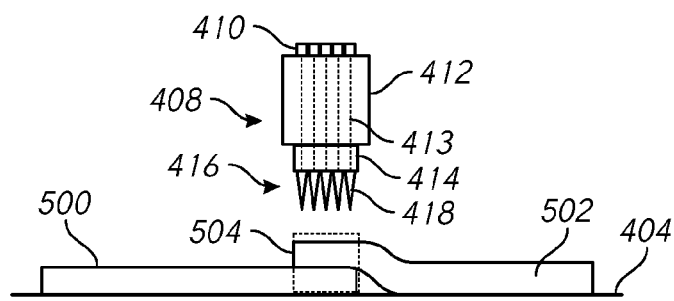
FIGS. 7A-7D show a side view of a process of high-frequency welding a pair of overlapping straps together.
Figure 7B:
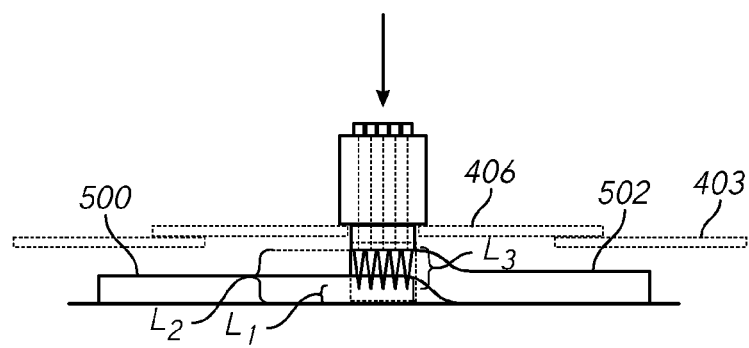
Figure 7C:
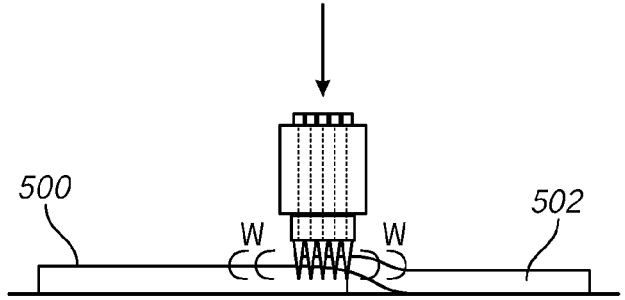
Figure 7D:
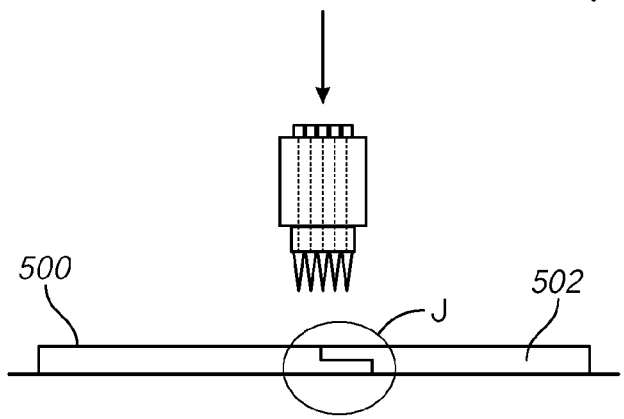

As shown in FIG. 7C, electromagnetic energy applied to the weld tool 408 is concentrated at the ends 418 of the pins 413, resulting in the generation of high-frequency alternating electric fields (represented using arcs W on either side of the contact surface 416). The electric fields cause polar molecules in the straps 502, 500 to oscillate and orient themselves with respect to the fields, which generates heat in the straps 502, 500 causing them to melt and fuse. Pressure applied using the contact surface 416 of the weld tool 408 (together with the press described elsewhere in this disclosure with reference to FIG. 4) promotes the formation of a weld joint J at the weld region 504. The weld tool 408 is then pulled away from the finished weld joint J (see FIG. 7D).

Figure 8A:
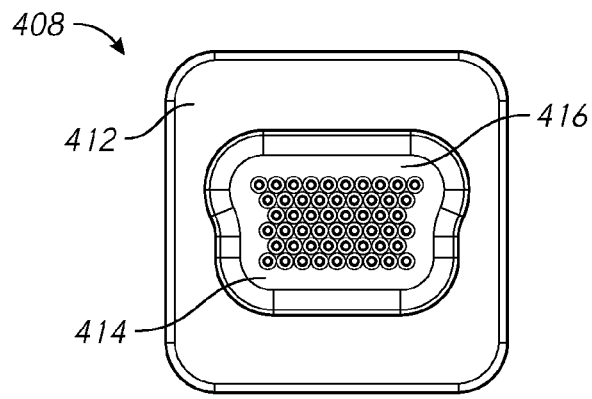
FIGS. 8A-8L show various views of weld tools for use in high-frequency welding.
Figure 8B:
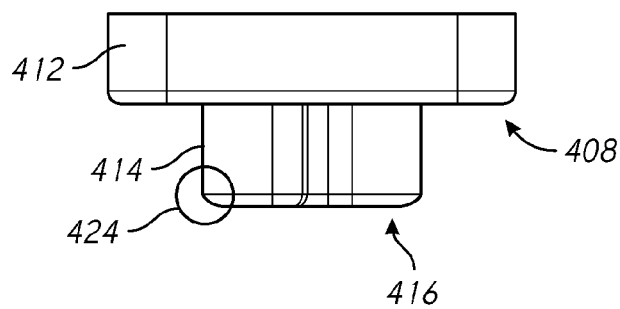
Figure 8C:
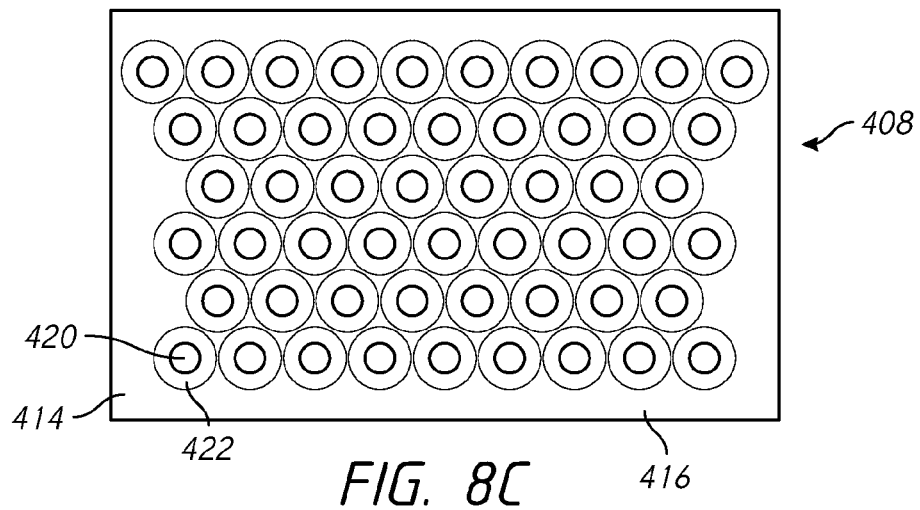

FIGS. 8A-8C show bottom, side, and bottom close-up views of a non-limiting exemplary weld tool 408. As shown in FIG. 8C, the contact surface 416 comprises apertures 420 adapted to hold the pins 413. The apertures 420 are defined by recesses 422 present in the contact surface 416. The recesses 422 can be crater-like, or can have substantially hemi-spherical or frustoconical geometry. The recesses 422 lie on portions of the contact surface 416 surrounding the pins 413 (particularly near the ends 418) in use. In the illustrated contact surface 416, the apertures 420 (and pins 413 in use) are arranged in rows such that consecutive or touching recesses 422 are present. The rows may be offset by about half of the distance between the centers of two adjacent apertures 420 of a given row. The offset is such that the rows are arranged in a honeycomb-like shape.

Figure 8D:
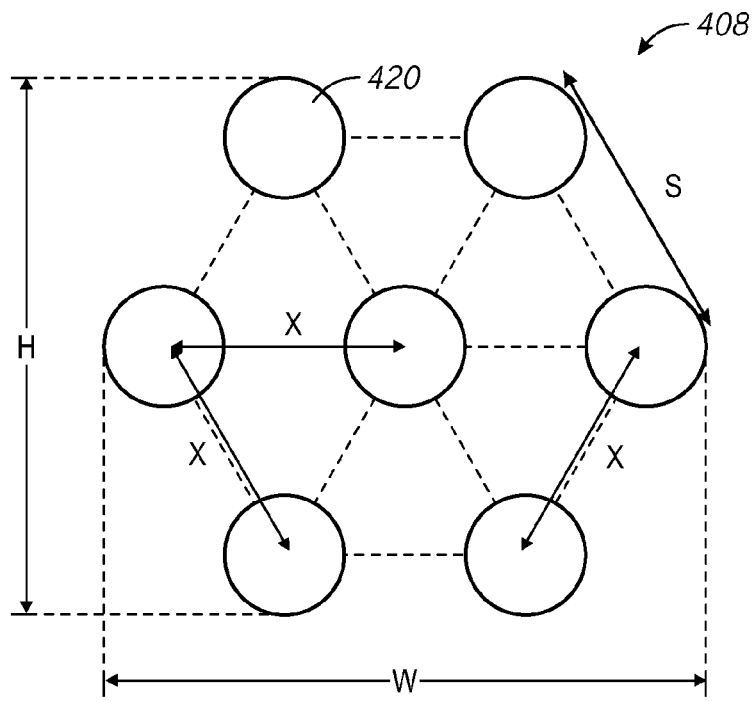

FIG. 8D illustrates a weld tool 408 having a similar aperture arrangement (recesses 422 not illustrated) as FIG. 8C. The apertures 420, which hold the pins 413 (not shown), are offset and spaced apart such that each aperture 420 is substantially equidistant from each adjacent aperture 420. As illustrated, six apertures 420 are arranged around a center aperture 420 in a hexagonal arrangement or honeycomb-like shape and spaced apart from each adjacent aperture 420 by a distance X. Each aperture 420 has a diameter D. Maintaining proper spacing of the apertures 420 (and ends 418 in use) can promote an even or balanced weld joint. Further, the hexagonal arrangement of the apertures 420 provides uniform weld strength and flex characteristics across the weld joint. Preferably, the distance X may be 1.0 mm and the diameter D may be 0.5 mm. However, the distance X and diameter D can, for example, be larger or smaller than shown and described with reference to the illustrated embodiment. In the illustrated configuration, the hexagonal arrangement has an overall height H of 2.232 mm and an overall width W of 2.5 mm. The apertures 420 are enclosed within a hexagonal-shaped area that surrounds the apertures 420. That is, the welding area of the weld tool 408 may be defined as a hexagonal-shaped area that surrounds the apertures 420. As illustrated, outer segments S that define the hexagonal-shaped area are tangent to outer edges of outermost adjacent pins 420. The segments S may have a length of 1.25 mm such that the total area of the hexagonal-shaped area is 4.06 mm$^2$. As such, seven apertures 420 having a diameter D of 0.5 mm provide a total aperture area of 1.374 mm$^2$. As each aperture 420 accommodates a pin 413 having a substantially identical diameter and area, a pin density percentage may be defined as a ratio percentage of pin area versus total welding area (i.e., hexagonal-shaped area). Therefore, a weld tool 408 having seven apertures 420 with diameters D of 0.5 mm, spaced apart by a distance X of 1.0 mm and arranged in a hexagonal arrangement having a total area of 4.06 mm$^2$, has a pin density percentage of 33.8%. Accordingly, a strap or material welded by the weld tool 408 with the illustrated hexagonal arrangement can have a weld joint that approximates the pin density. In the instant example, the pin density is 33.8%, which may result in the weld joint having approximately 33.8% melted welded material within the weld area or pin area. The actual portion of melted material within the weld or pin area can vary based on relevant factors of the welding process (e.g., weld power, weld time, materials being welded, etc.). Thus, the actual portion of melted material may differ from the pin density, but will likely fall within a range the approximates the pin density (e.g., within 5%, 10%, 20% or 25% of the pin density). A weld joint having a higher pin density percentage provides a less flexible weld joint than a weld joint having a lower pin density percentage. This is because more of the weld joint will include melted welded material which is relatively rigid and inflexible. As a result, there will be less fabric between each of the weld points that has not been melted and is still able to be flexed or stretched, thereby, allowing the strap or material to stretch. In alternative configurations, the apertures 420 may have a diameter D between 0.1 to 1.0 mm. As such, decreasing the diameter D of the aperture 420 (and the pin 413) will decrease the pin density percentage and result in a weld joint with more flexibility and/or stretch while larger diameters will provide less flexibility and/or stretch. Accordingly, the diameter D and/or distance X may be varied according to the amount of flex or stretch desired by the weld joint.

Figure 8E:
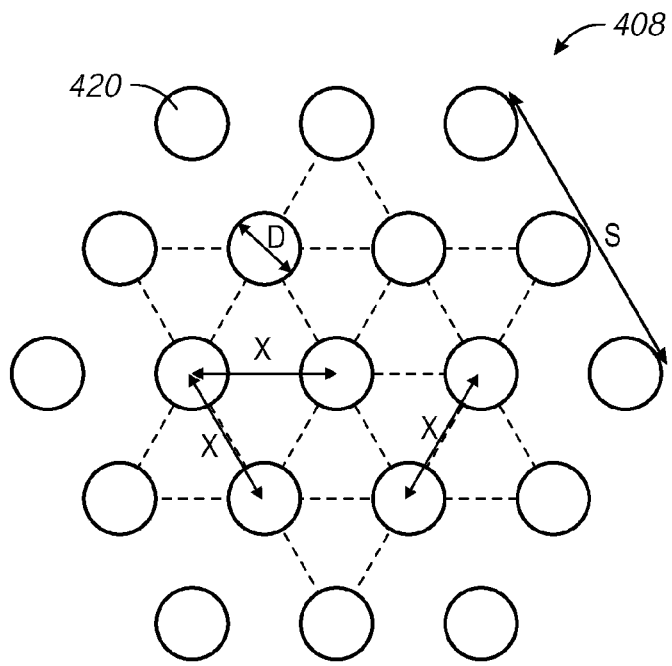

FIG. 8E illustrates a similar hexagonal arrangement as FIG. 8D with identical aperture diameters D and distance X between apertures 420. FIG. 8E differs by having nineteen total apertures 420 with the apertures 420 arranged in two concentric hexagons around a center aperture 420. As such, due to the increased number of apertures 420, the hexagonal arrangement has segments S with a length of 2.25 mm such that the total area of the hexagonal-shaped area 13.15 mm$^2$. Therefore, a weld tool 408 having nineteen apertures 420 with diameters D of 0.5 mm and that are arranged in a hexagonal arrangement, has a pin density percentage of 28%. Thus, compared to the pin density percentage of 33.8% provided by the seven apertures 420 in the hexagonal arrangement in FIG. 8D, the pin density percentage decreases as the number of apertures 420 and the overall hexagonal-shaped area increases.

Figure 8F:
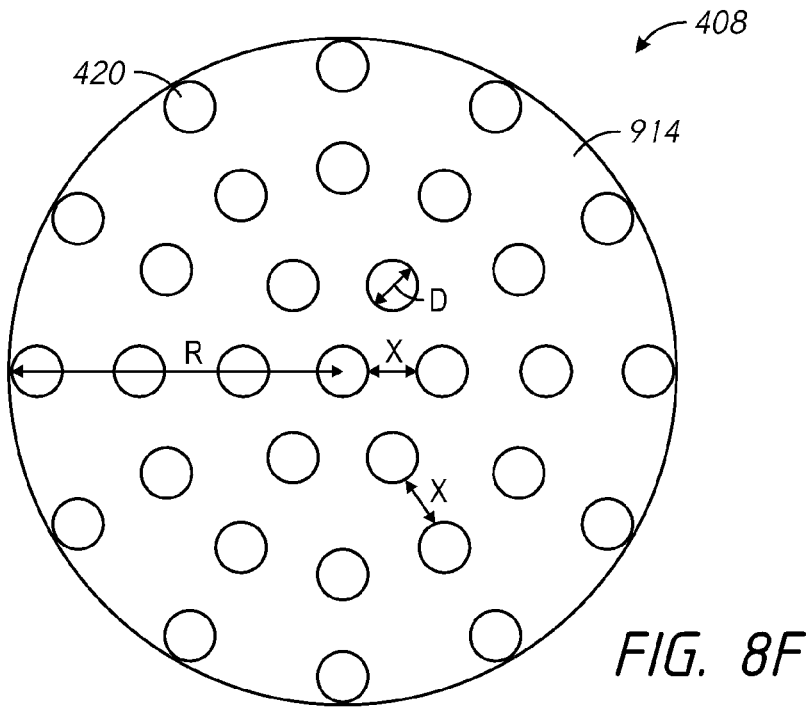

FIG. 8F illustrates a weld tool 408 having a radial arrangement with thirty-one apertures 420 arranged in three concentric circles around a center aperture 420. Each aperture 420 has a diameter D of 0.5 mm. The distance X between each aperture 420 in the radial direction is 0.5 mm. The total radial distance R from the center aperture 420 to a radially-outermost point of the outermost apertures 420 is 3.25 mm, which defines a circular-shaped area with a total area of 33.18 mm$^2$. Therefore, a weld tool 408 having thirty-one apertures 420 arranged in three concentric circles, spaced apart a distance X of 0.5 mm and having a diameter D of 0.5 mm, has a pin density percentage of 18%. Further, as illustrated, the circumferential distance between adjacent apertures 420 increases as the distance from the center of the weld joint increases. Accordingly, the flexibility of the weld joint will be greater in regions further away from the center of the weld joint. Therefore, the radial aperture arrangement in FIG. 8F provides different strength and flexibility characteristics compared to the hexagonal aperture arrangements in FIG. 8A-8E. In other configurations, the outermost apertures 420 may have an ovular or elongated shape to reduce the circumferential distance between adjacent apertures 420 and provide additional strength to the regions further from the center of the weld joint.

Figure 8G:
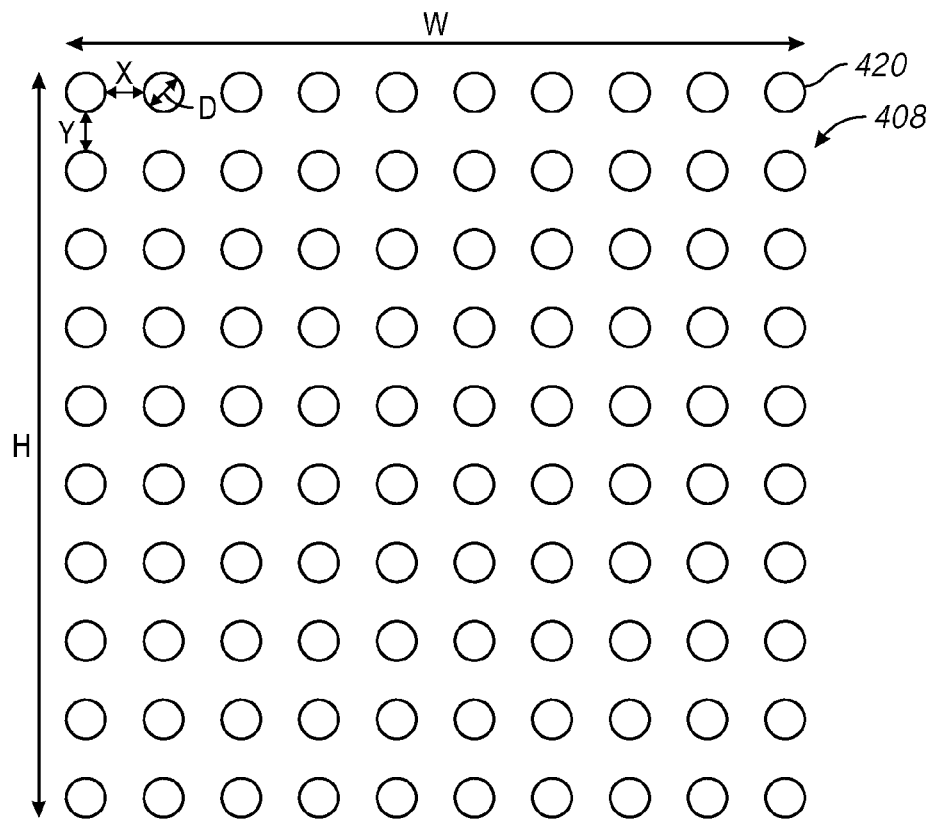

FIG. 8G illustrates a weld tool 408 having a square grid aperture arrangement with one hundred apertures 420 aligned in ten rows having ten apertures 420 per row. Each aperture 420 is spaced apart from each adjacent aperture 420 by distances X, Y of 0.5 mm. Each aperture 420 has a diameter D of 0.5 mm. As such, the diameter D and distances X, Y of the apertures 420 have a 1:1 relationship. The square grid arrangement has a height H and width W of 9.5 mm. Therefore, a weld tool 408 having one hundred apertures 420 with a diameter D of 0.5 mm and arranged in the square grid arrangement illustrated in FIG. 8G, has a pin density percentage of 21.71%. In alternative configurations, the diameter D may have a value of 0.1 to 1.0 mm and distance X may have a value different than the distance Y with values between 0.1 to 5.0 mm.

Figure 8H:
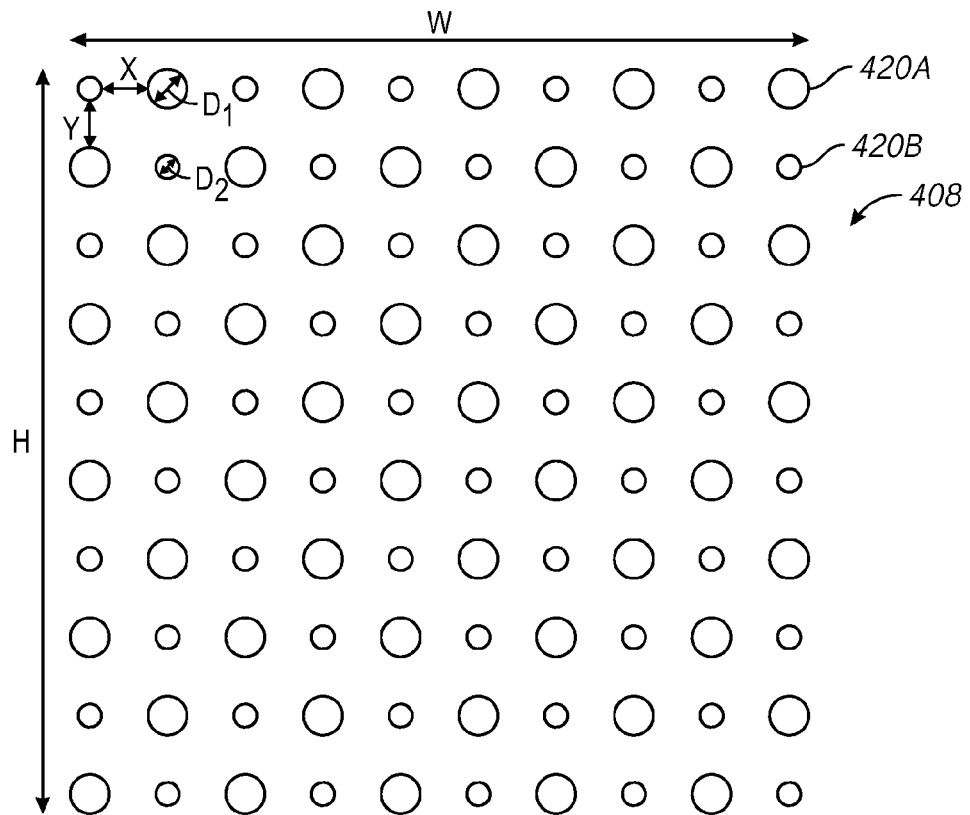

FIG. 8H also illustrates a weld tool 408 having a square grid arrangement with one hundred apertures 420A, 420B aligned in ten rows having ten apertures 420A, 420B per row. However, in contrast to FIG. 8G, the square grid arrangement includes large apertures 420A and small apertures 420B which are alternatingly disposed along the length of each row. The large apertures 420A have a diameter $D_1$ of 0.5 mm and the small apertures 420B have a diameter $D_2$ of 0.25 mm. Each aperture 420A, 420B is spaced apart from each adjacent aperture 420A, 420B by distances X, Y of 0.625 mm. The square grid arrangement has a height H and width W of 9.5 mm. Therefore, a weld tool 408 having fifty large apertures 420A and fifty small apertures 420B arranged in a square grid arrangement as illustrated in FIG. 8H, has a pin density percentage of 13.59%. Thus, compared to the pin density percentage of 21.71% provided by the square grid aperture arrangement in FIG. 8G, the square grid arrangement having apertures 420A, 420B with large and small diameters $D_1$, $D_2$ may provide a weld joint with greater flexibility. In alternative configurations, the diameter D may have a value of 0.1 to 1.0 mm and the distance X may have a value different than the distance Y with values between 0.2 to 5.0 mm.

Figure 8I:
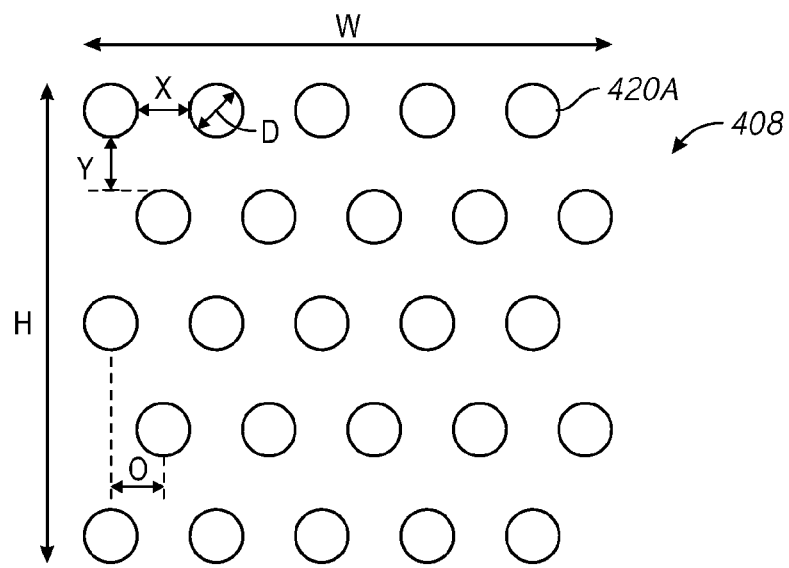

FIG. 8I also illustrates a weld tool 408 having a grid arrangement with apertures 420 arranged in rows having five apertures 420 per row. However, in contrast to FIGS. 8G and 8H, each row is offset by a distance O from each adjacent row. Preferably, the offset distance O is 0.5 mm. Each aperture 420 is spaced apart from each adjacent aperture 420 by distances X, Y of 0.5 mm and each aperture 420 has a diameter D of 0.5 mm.

As such, the diameter D and the distances X, Y of the apertures 420 have a 1:1 relationship. The square grid arrangement has a height H and width W of 5.0 mm. Therefore, a weld tool 408 having twenty-five apertures 420 with a diameter D of 0.5 mm and arranged in a grid arrangement with offset rows, has a pin density percentage of 20%. Put another way, the grid arrangement has one aperture 420 for every 1 mm$^2$. In alternative configurations, the diameter D may have a value of 0.1 to 1.0 mm and the distance X may have a different value than the distance Y with values ranging between 0.2 to 5.0 mm. Further, in some configurations, the offset distance O may be determined by the following equation: O=(X+D)/2.

Figure 8J:
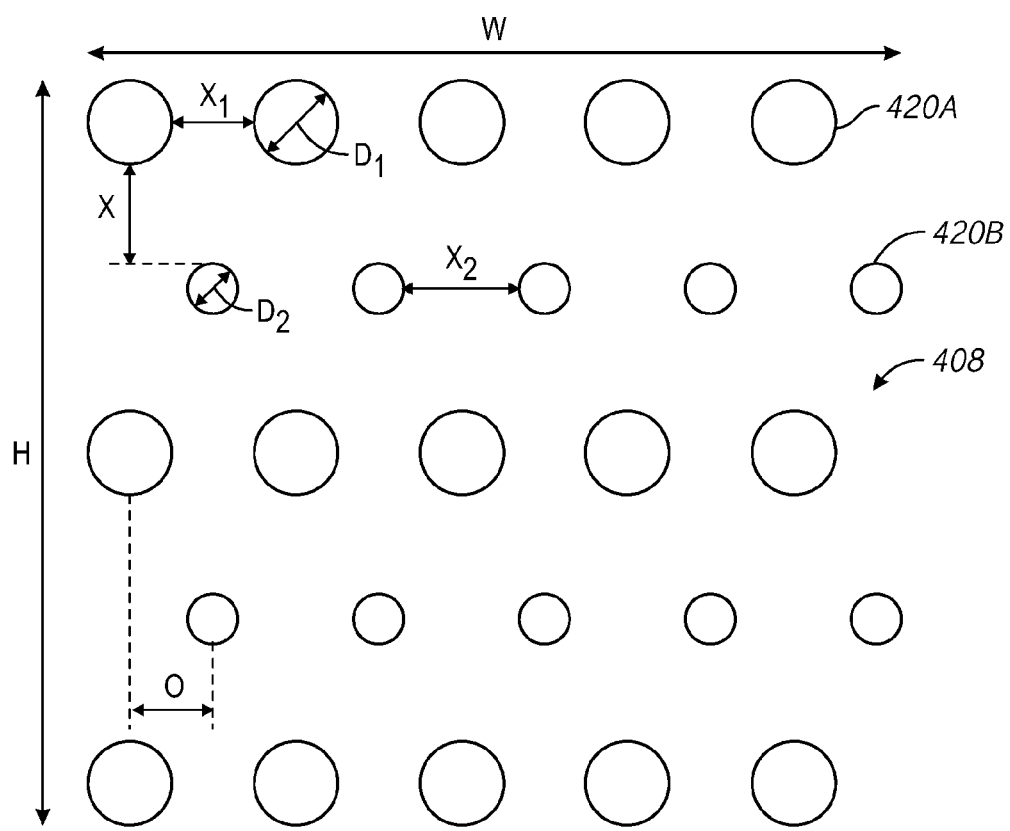

FIG. 8J also illustrates a weld tool 408 having a grid arrangement with offset rows. However, in contrast to FIG. 8I but similar to FIG. 8H, the grid arrangement includes large apertures 420A and small apertures 420B which are disposed in alternating rows. The large apertures 420A have a diameter $D_1$ of 0.5 mm and the small apertures have a diameter $D_2$ of 0.25 mm. Each large apertures 420A is spaced apart a distance $X_1$ of 0.5 mm from each adjacent large apertures 420A. Each small aperture 420B is spaced apart a distance $X_2$ of 0.75 mm from each adjacent small aperture 420B. Each row is offset by a distance O of 0.5 mm from each adjacent row. The grid arrangement has a height H of 5.0 mm and a width W of 4.875 mm. Therefore, a weld tool 408 having a bottom section 414 with twenty-five apertures 420 with diameters $D_1$, $D_2$ and arranged in a grid arrangement with offset rows, has a pin density percentage of 14%. Thus, compared to the pin density percentage of 20% provided by the aperture arrangement in FIG. 8I, the aperture arrangement having apertures 420A, 420B with large and small diameters $D_1$, $D_2$ may provide a weld joint with greater flexibility.

For the aperture arrangements disclosed, the pin density percentage can be within a range of 10-50%. The pin density percentage may depend upon the region of the headgear where straps are joined since consideration must be given to the desired strength and flexibility for that region of the headgear. In some configurations, the pin density percentage can be within the range of 15-35%. Preferably, the pin density percentage is between 15-25%.

Figure 8L:
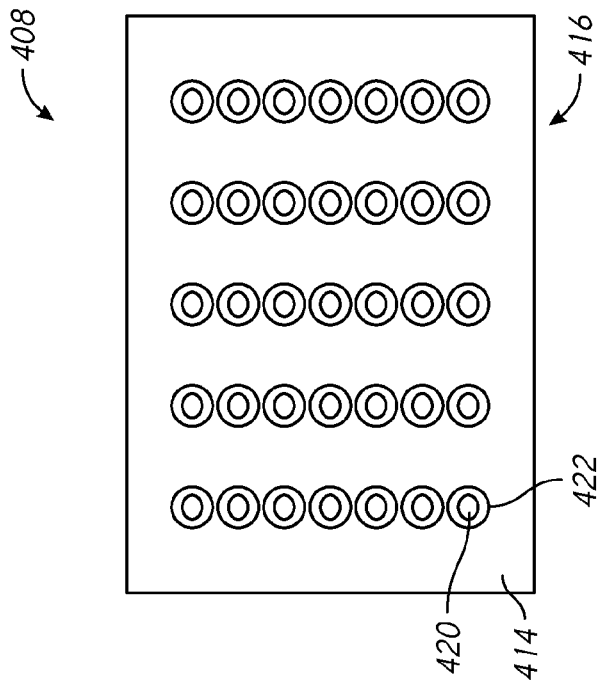
Figure 8K:
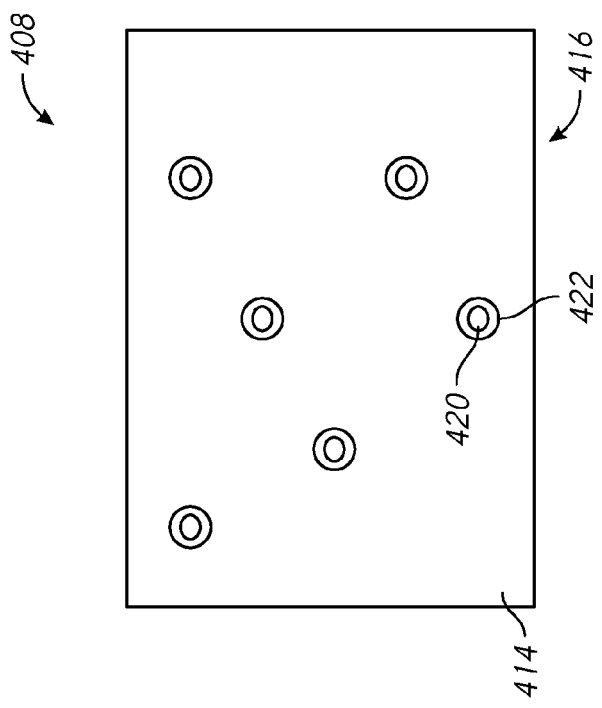

In other configurations, the apertures 420 (and pins 413 in use) may be arranged according to other shapes or patterns, including, but not limited to, sine wave, square wave, or zig-zag shapes. In other configurations, the distance of each aperture 420 from adjacent apertures 420 can be irregular or inconsistent over the contact surface 416. For example, and as illustrated in FIG. 8K, the apertures 420 may be randomly scattered over the contact surface 416. In other configurations, the apertures 420 can be arranged in rows. For example, and as illustrated in FIG. 8L, the apertures 420 may be arranged in vertical rows along the contact surface 416. Arranging the apertures 420 in rows can allow for a relatively strong weld at the finished weld joint while allowing for flexing or bending at the weld joint in one or more axes (e.g. preferential bending).

As shown in FIG. 8C, the contact surface 416 comprises beveled edges 424. In some configurations, the edges 424 could be rounded or arcuate. Beveling or rounding the edges of the contact surface 416 lessens concentrations of energy on the edges of the weld region 504. This can promote a more even or balanced weld joint and lessen chances of excessive melting or burning in undesired places. In other configurations, the contact surface 416 may comprise straight edges.

FIGS. 9A-9B show a cross-section of a non-limiting exemplary recess 422 in more detail. The recess 422 is inwardly chamfered (in contrast with the straight edge 421 shown in FIG. 10). The inwardly chamfered recess 422 is curved or substantially arcuate. The arcuate recess 422 can help prevent undesired concentrations of electromagnetic energy along portions of the contact surface 416, which can minimize the chance of excessive melting or burning of the top strap 502 in use. In other configurations, the recess 422 can have straight edges. In other configurations, and as described elsewhere in this disclosure, beveled recesses 422 may also be used. The illustrated recess 422 is substantially crater-like. The curvatures of the sides of the crater-like recess 422 are defined by substantially circular cross-sections of the weld tool 408 (as shown by circle c in the close-up shown in FIG. 9B). In the illustrated configuration, the circle c comprises a radius r=0.6 mm or about 0.6 mm. In other configurations, the radius may, for example, be in the range of about 0.2 mm to about 1.0 mm, or about 0.3 mm to about 0.9 mm, or about 0.4 mm to about 0.8 mm, or about 0.5 mm or about 0.7 mm. In some configurations, the circle c has a radius r selected to give the contact surface 416 of the weld tool 408 a shape that allows for energy to be efficiently transferred to the weld region 504. In some configurations, the curvatures of the sides of the crater-like recesses are defined by substantially circular cross-sections of the weld tool having radii x that are proportional to the average distance between pins y according to the ratio x:y. In some such configurations, the ratio x:y can be in the range of 0.3 to 0.4, or about 0.3 to about 0.4. In other configurations, the ratio x:y can be in the range of about 0.2 to about 0.5, or about 0.25 to about 0.45.

Figure 11:
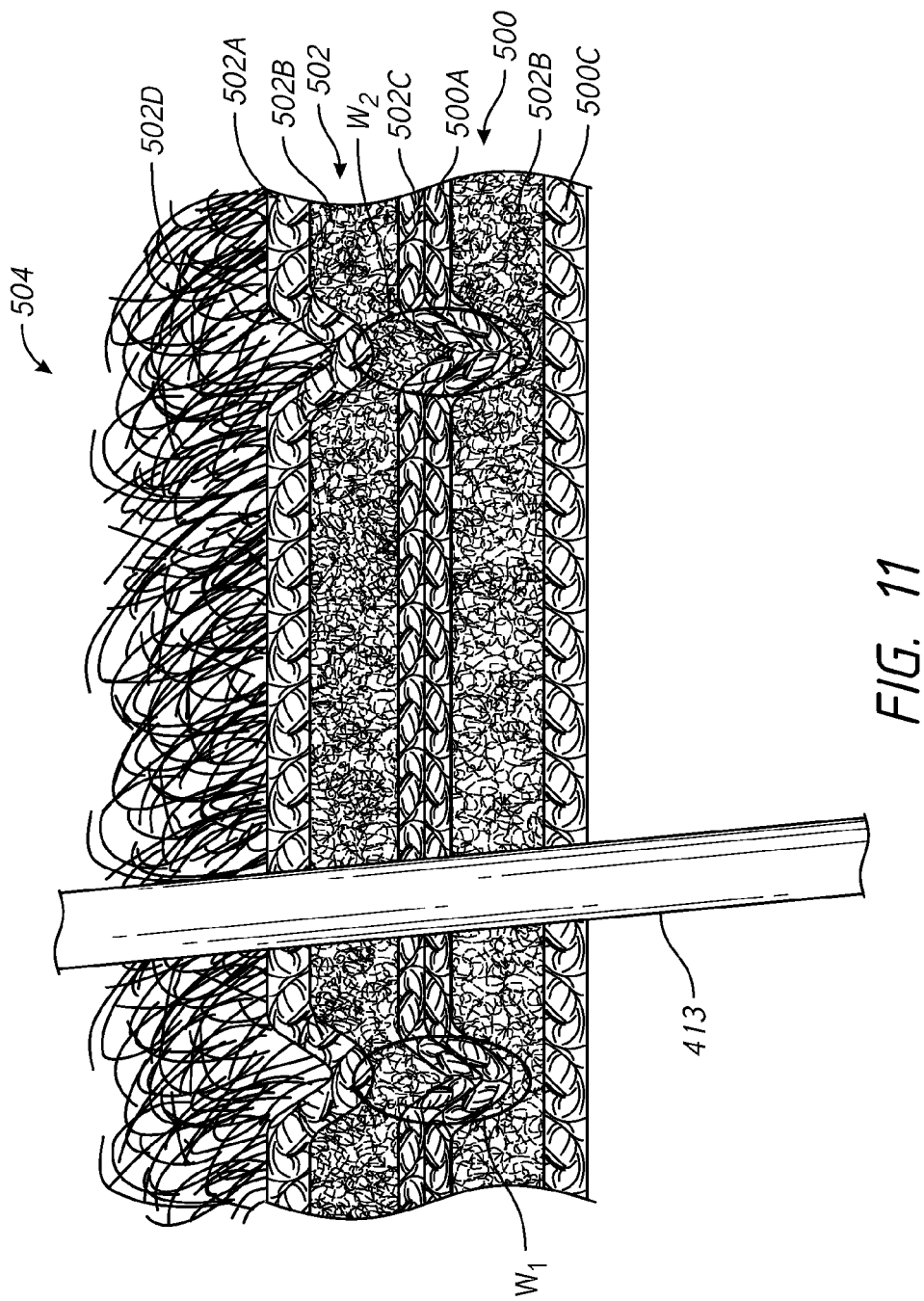
FIG. 11 shows a close-up cross-sectional view of a pair of welded straps.

FIG. 11 shows a close up cross-sectional view of straps welded at a pair of weld points $W_1$, $W_2$ using a pin 413 as a reference. The pin 413 has a width of 0.5 mm or about 0.5 mm. As can be seen, the illustrated non-limiting exemplary top and bottom straps 502, 500 each comprise several layers. The top strap 502 comprises cloth or fabric layers 502A, 502C (hereinafter generally referred to as cloth layers) comprising hairs 502D that project outwardly from the layers 502A, 502C. The hairs 502D may act as a hooked surface that can engage with, for example, the loop patches 316, 314, 312, 310 described elsewhere in this disclosure with reference to FIGS. 2A-2B. The cloth layers 502A, 502C sandwich a foam layer 502B. Similarly, the bottom strap 500 comprises cloth layers 500A, 500C sandwiching a foam layer 500B. Hairs extending from the bottom fabric layer 502C of the top strap 502 and hairs extending from the top fabric layer 500A of the bottom strap 500 to at least some extent interweave and compress against one another when the straps are overlaid to form the weld region 504, facilitating the formation of a weld joint. As can be seen, use of the disclosed welding methods, tools, apparatus and systems can promote a weld while mitigating the presence of visible bulges or burns. Additionally, the use of a weld tool 408 comprising pins 413 that protrude into the straps 502, 500 can reduce or eliminate the formation of witness marks (e.g., marks created by detailing on the contact surface 416 of the weld tool 408, including, but not limited to, ridges or recesses) on the finished weld joints. Witness marks may be caused when the fabric is melted and the straps 502, 500 are fused together to become a solid plastic region that includes a portion of a visible surface of the fabric. It may be undesirable in some headgear for there to be regions of reduced flexibility and/or elasticity on or near a visible surface of the fabric (e.g., aesthetic appeal, user comfort, etc.).

Although the illustrated embodiments show that the weld tool 408 comprises pins 413 that are positioned over the weld base 402, in some configurations, the weld base 402 may comprise the pins 413 and the weld tool 408 may primarily serve to exert pressure against the weld region 504. In some configurations, both the weld tool 408 and the weld base 402 may comprise pins 413. For example, pins extending from the weld tool 408 may penetrate the straps 502, 500 on one half of the weld region 504 and pins extending from the weld base 402 may penetrate the straps 502, 500 on the other half of the weld region 504. In some configurations, the weld tool 408 can be secured to the weld base 402 and the weld press alone (described elsewhere in this disclosure with reference to FIG. 4) can be used to apply pressure to the straps 502, 500.

Although the illustrated embodiments show that two overlapping sections of material (e.g. straps) can be welded, in some configurations, a greater number of sections can be welded. For example, in some configurations 3, 4 or 5 straps can be welded together using the methods, apparatus, tools and systems disclosed. In some configurations, the weld tool 408 can comprise pins 413 that penetrate all of the sections of material. For example, three overlapping headgear straps (being called top, middle and bottom straps) may be welded using a weld tool 408 having pins 413 that penetrate the entire depth of the top and middle straps and a portion of the bottom strap. In other configurations, the pins 413 may be of variable length to promote adequate weld strength between straps along each strap interface. For example, if three overlapping headgear straps are used, a weld tool 408 having pins 413, a portion of which penetrate the full depth of the top strap and a portion of the middle strap, another portion of which penetrate the full depth of the top and middle straps and a portion of the bottom strap, may be used.

Figure 12:
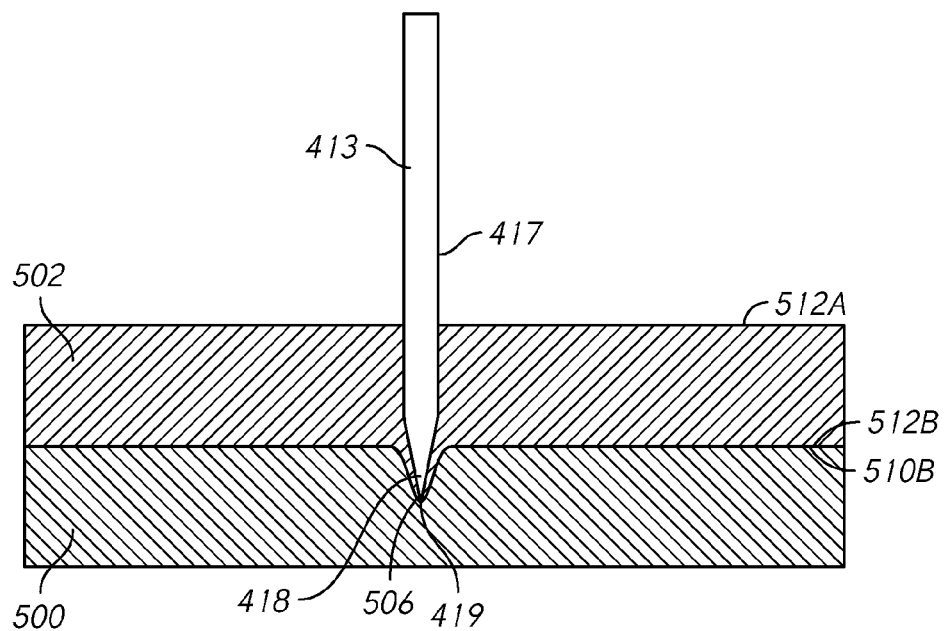
FIG. 12 shows a close-up view of a cross-section of straps and a pin having pointed tip.

FIG. 12 is a close-up cross-sectional view of a pin configuration which reduces or eliminates the formation of witness marks on the finished weld joints. The pin 413 has an elongate portion 417 that extends in a direction away from the weld tool (not shown) toward a pin end 418 that is opposite the weld tool (not shown). As illustrated, the elongate portion 417 narrows at the pin end 418 to form a pointed tip 419. To weld the straps 502, 500 together, the pointed tip 419 pierces an outer surface 512A and penetrates entirely through the top strap 502. As opposed to applying pressure directly to the outer surface 512A, piercing the outer surface 512A causes the outer surface 512A to remain substantially undeflected (i.e., the outer surface 512A is not pressed closer to the inner surfaces 512B, 510B). As illustrated, while penetrating through the top strap 502, the pin 413 presses the inner surface 512B of the top strap 502 against the inner surface 510B of the bottom strap 500. While the inner surfaces 510B, 512B are compressed, electromagnetic energy is applied to the pin 413 which generates heat that causes the straps 502, 500 to melt around the weld point 506, thereby, fusing the straps 502, 500 together. However, since the outer surface 512A remains undeflected, the outer surface 512A will not be joined in the weld. Accordingly, a visible witness mark will not be formed on the outer surface 512A. In other configurations, it is possible that a portion of the pointed tip 419 may exit and extend through the inner surface 512B of the top strap 502. However, despite the pin end 418 penetrating through the inner surface 512B, the pointed tip 419 may still press the inner surface 512B of the top strap 502 against the inner surface 510B of the bottom strap 500. It should be understood that the shape and geometry of the elongate portion 417 and pointed tip 419 may vary according to the thickness and type of strap material, quantity and geometry of the pins, desired weld strength, etc.

Figure 13:
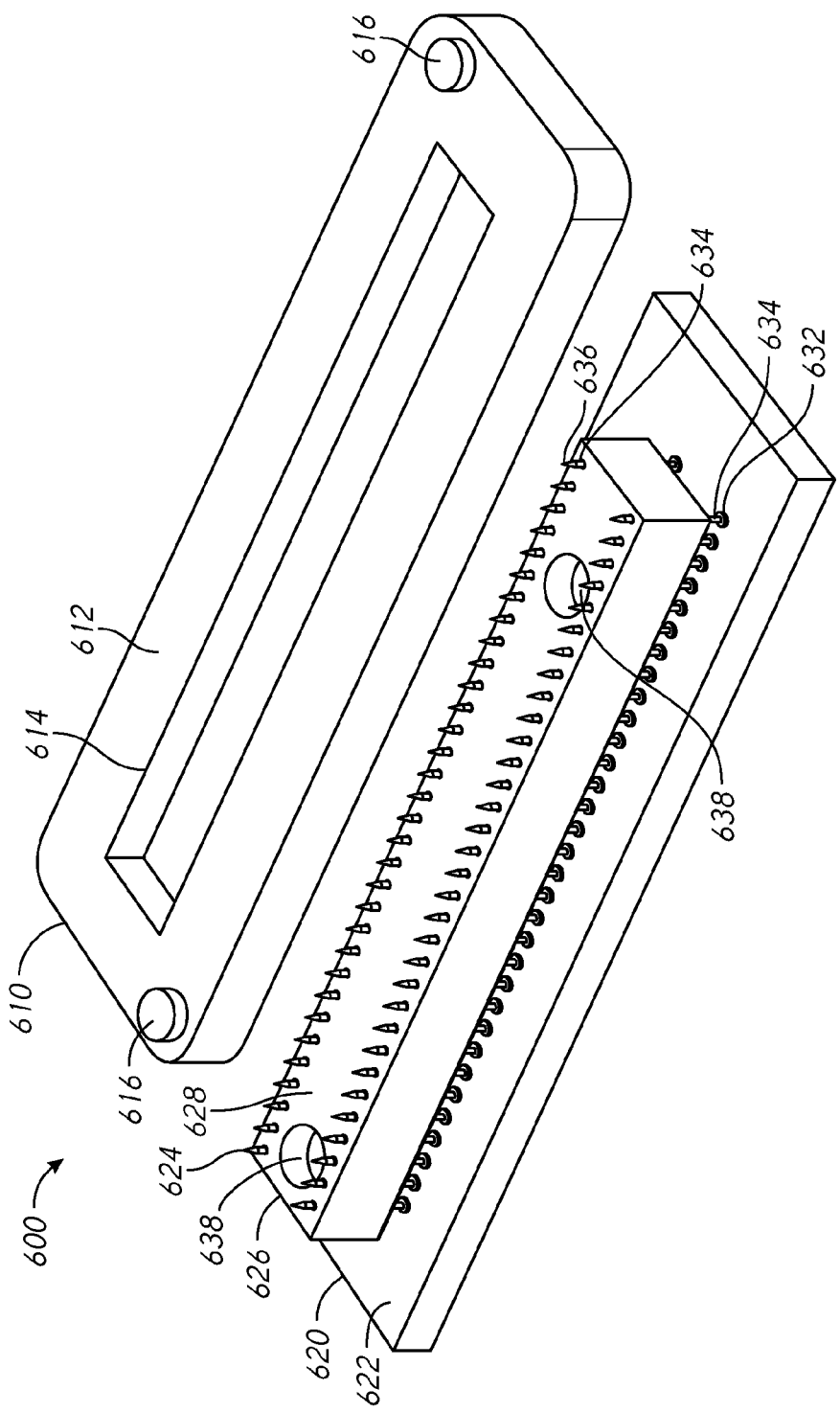
FIG. 13 shows a plan view of a high-frequency welding system.
Figure 14:
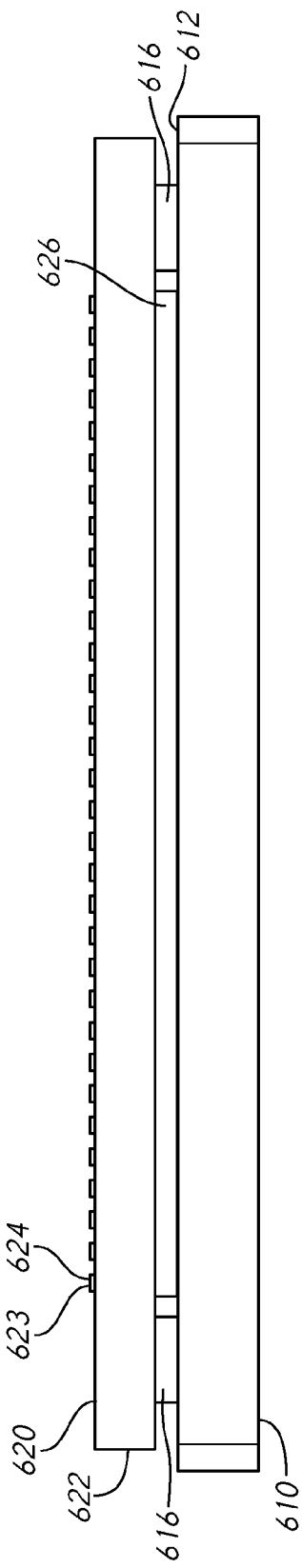
FIG. 14 shows a side view illustrating the weld tool inserted into the weld base of the high-frequency welding system.
Figure 15:
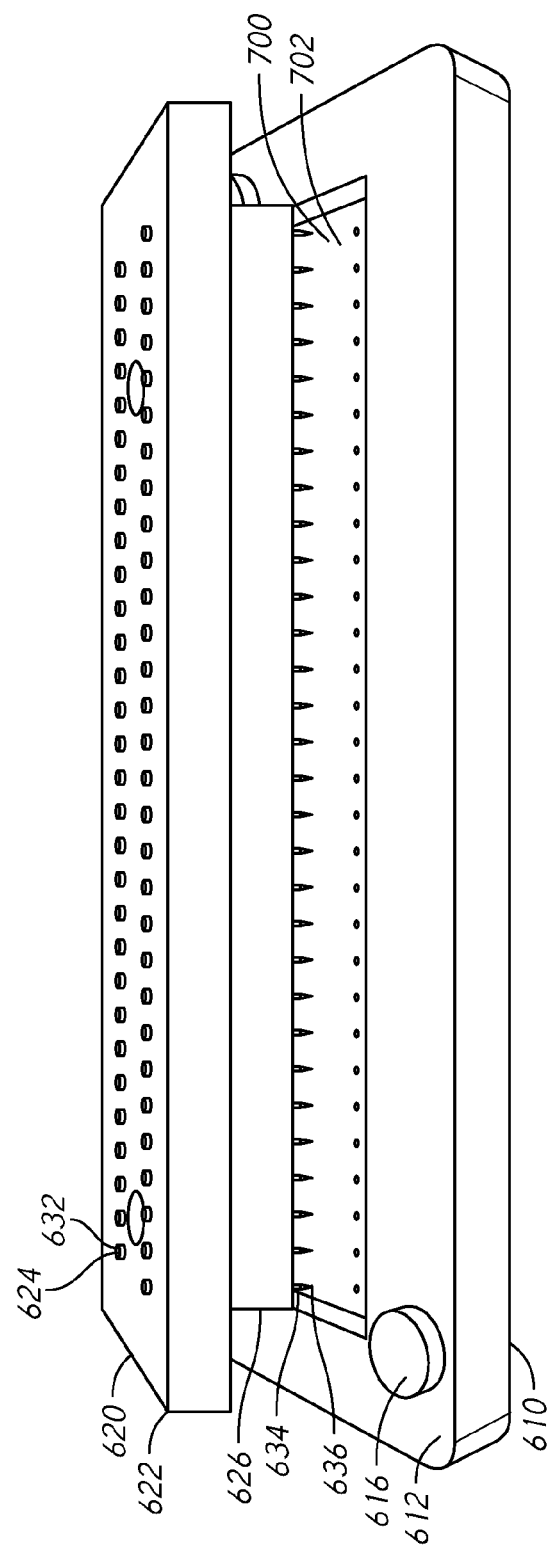
FIG. 15 shows a side view illustrating the weld tool partially inserted into the weld base of the high-frequency welding system.

FIGS. 13-15 illustrate a high frequency welding system 600 that may further reduce or eliminate the formation of a witness mark and form a weld joint that does not significantly effect or that preserves a substantial amount of the flexibility and/or elasticity of the fabric. The welding system 600 comprises a weld base (e.g., anvil) 610 and a weld tool 620. The weld base 610 includes a top surface 612 and a positioning cavity 614 that is recessed below the top surface 612 and adapted to hold the top and bottom sheets of material 702, 704 in overlapping alignment prior to forming the strap 700 of the headgear. The weld tool 620 includes a top plate 622, pins 624 and an insert portion 626. The pins 624 are positioned within and extend through both the top plate 622 and the insert portion 626 such that the top plate 622 is connected to the insert portion 626 via the pins 624. The weld tool 620 may also have bosses 638 positioned between the top plate 622 and the insert portion 626 to connect the top plate 622 to the insert portion 626. In some configurations, the insert portion 626 may slide axially along the lengths of the pins 624 and the bosses 638.

The pins 624 are substantially straight and include a head portion 632, an elongate portion 634 and a tip portion 636. The head portion 632 is positioned within the top plate 622 and extends entirely through the top plate 622. An upper region of the head portion 632 may protrude from the top plate 622 to provide a connection with an energy source (not shown). The elongate portion 634 is connected to the head portion 632 and extends perpendicularly outward from the top plate 622 in a direction that is parallel to the insertion direction of the insert portion 626 into the positioning cavity 614, as will be discussed in greater detail below. The elongate portion 634 extends entirely through the insert portion 626 such that elongate portion 634 protrudes outward from a surface 628 of the insert portion 626 that is opposite the top plate 622 and that faces the positioning cavity 614. The tip portion 636 is positioned at the end of the elongate portion 634 that protrudes outwardly from the insert portion 626. The elongate portion 634 and the tip portion 636 may protrude a distance from the surface 628 of the insert portion 626 according to the desired depth of penetration of the bottom sheet 704 (if any) and clearance, as previously disclosed. The elongate portion 634 of the pins 624 may have a diameter of 0.3 mm to 1 mm and the tip portion 636 may narrow to a point. The pins 624 may be spaced apart by a distance of 2.5 mm to 6 mm (i.e., between the centers of the pins 624) arranged in a single-file row along an outer edge of the surface 628 of the insert portion 626. The pins 624 may be arranged in single-file rows that are aligned according to the direction of stretch of the finished product, which will be discussed in greater detail below. It should be noted that the welding system 600 is not limited to pins 624 arranged in single file rows and may be arranged according to any of the aperture/pin arrangements previously disclosed.

As illustrated in FIGS. 14 and 15, the top plate 622 may be joined with the weld base 602 such that the top plate 622 rests on top of the weld base 602 and the insert portion 626 is able to be inserted into the positioning cavity 614. The insert portion 626 has a size and shape that corresponds with the shape of the positioning cavity 614. Spacers 616 may be attached to the weld base 610 and/or the weld tool 620 to limit axial motion (i.e., the direction parallel to the insertion direction) between the weld base 610 and the weld tool 620 when the insert portion 626 is inserted into the positioning cavity 614. The spacers 616 may be arranged to provide the desired clearance and depth of penetration (if any) into the bottom sheet 704, as previously disclosed.

The weld base 610, the top plate 622 and/or the insert portion 626 may be a non-conductive tool and/or formed from an insulating material, such as plastic, to reduce or minimize heat or energy transferred from the surface 628 of the insert portion 626 to the top and bottom sheets of material 702, 704, thereby, further reducing or preventing the formation of a witness mark. Preferably, at least the weld base 610 and insert portion 626 (or other portions that contact the sheets 702, 704) are constructed from or comprise an insulating material. Therefore, the only heat or energy transferred to the top and bottom sheets 702, 704 are substantially provided by the pins 624. In some configurations, any one or all of the top plate 622, the pins 624 or the insert portion 626 may be formed from a non-insulating material, such as metal. However, with such a configuration, a thermally insulating material or coating may be applied to the surface 628 to reduce or minimize heat transferred from the surface 628 of the insert portion 626 to the top and bottom sheets 702, 704. The non-conductive or insulating material can be selected in view of the type or particulars of the weld process. For example, the tool can be configured to reduce thermal conductivity or reduce electrical or electromagnetic conduction. The tool may be formed from a material that prevents or reduces thermal conductivity, electrical conductivity, or electromagnetic conductivity.

In operation, the strap 700 may be formed by inserting the top and bottom sheets 702, 704 into the positioning cavity 614. The top and bottom sheets of material 702, 704 may be inserted and arranged in an overlapping relationship. It should be understood that 'top' and 'bottom' as used in this disclosure can be interpreted as referring to positioning with respect to the high frequency welding system 600 rather than with respect to gravity. The weld tool 620 is positioned onto the weld base 610 such that the insert portion 626 is inserted into the position cavity 614. A compressive force is applied to the top plate 622 of the weld tool 620. Accordingly, the pins 624 and the insert portion 626 contact and apply pressure to the top and bottom sheets 702, 704. The tip portion 626 of the pins 624 penetrate the entire depth of the top sheet 702 and partially penetrate the bottom sheet 704. The weld tool 620 is energized with electromagnetic energy (using an energy source, not shown), causing the pins 624 to generate alternating electric fields that cause polar molecules in the straps of material to oscillate and orient themselves with respect to the field. This movement of the polar molecules generates heat, causing a temperature increase that result in the melting of the sheets. Although the positioning cavity 614 and the insert portion 626 shown are rectangular, it should be understood that the positioning cavity 614 and the insert portion 626 could be formed in other shapes, for example, shapes which correspond to geometries of the straps to be welded. Further, the pins 624 are illustrated as having an elongate cylindrical shape. However, it should be understood that the pins could be formed in shapes (e.g., rectangular, ovular, etc. in cross-section) according to the desired strength and flexibility provided by the strap.

Figure 16A:
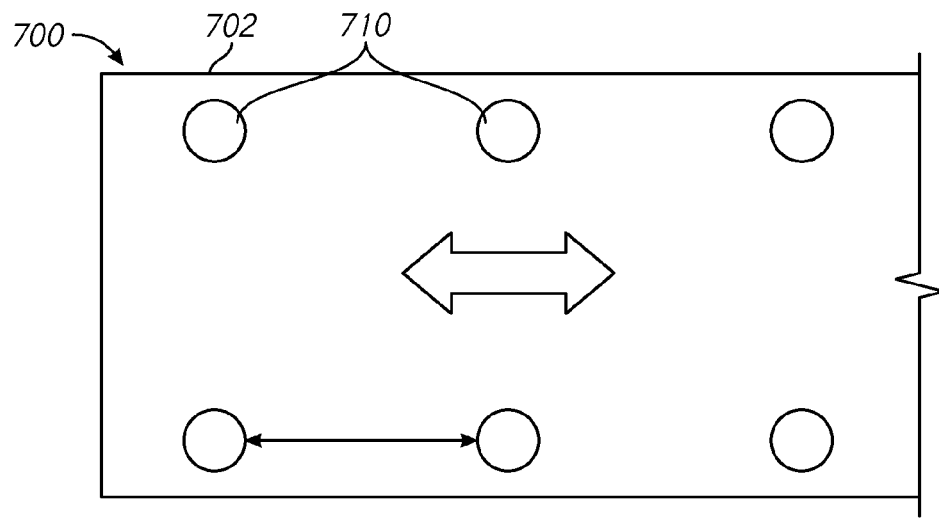
FIGS. 16A-16D show a headgear strap welded by the high-frequency welding system.

FIGS. 16A-16D illustrate the strap 700 after the sheets 702, 704 have been welded together by the high frequency welding system 600. As shown in FIG. 16A, the strap 700 has linearly spaced weld points 710 that are equidistantly spaced apart along the length of the strap 700. In contrast to a strap having a continuous seam weld, the weld points 710 are spaced apart such that the weld region formed by a single pin does not merge with a weld region from another pin. The weld points 710 provide a discontinuous weld such that the strap 700 can be stretched in a direction parallel to the direction of the linearly spaced weld points 710. Each of the weld points 710 may be spaced apart from an adjacent weld point 710 by a distance of 3.5 mm (i.e., in a neutral un-stretched position of the strap 700), which also corresponds to the spacing between the pins 624. Depending upon the amount of desired stretch and flexibility by the strap 700, the distance between weld points 710 (i.e., distance between the centers of each weld points 710) may be within a range of 2.5 mm to 6.0 mm. Accordingly, a greater distance between weld points 710 will provide a greater amount of stretch and flexibility. However, significantly larger distances between weld points 710 may be undesirable because the edges of the strap 700 may split or bow outward (i.e., the sheets 702, 704 may separate) between the weld points 710 when the strap 700 is either bent or turned inside out.

Figure 16B:
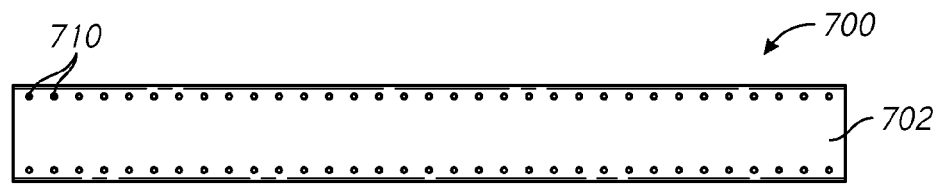
Figure 16C:
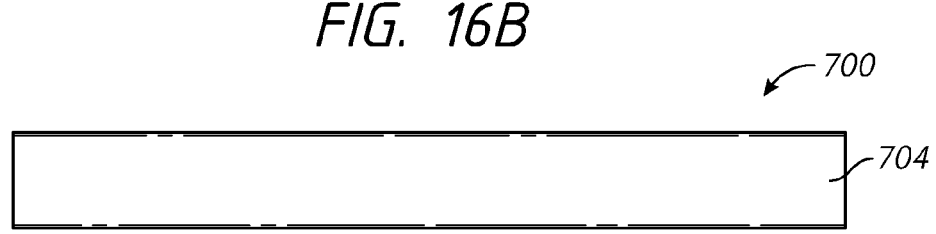
Figure 16D:
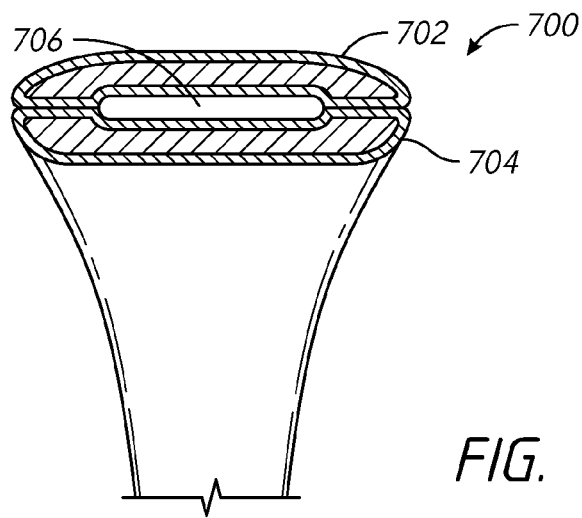

As shown in FIG. 16B, the weld points 710 may be visible when viewing the top sheet 702 of the strap 700 from a top-down view. However, as shown in FIG. 16C, the weld points 710 are concealed within the strap 700 and not visible when viewing the bottom sheet 704 of the strap 700 from a top-down view. FIG. 16D illustrates a cross-sectional view of the strap 700. As the pins 624 are arranged in single file rows along the outer edges of the top and bottom sheets 702, 704, the weld points 710 are positioned along the outer edges of the top and bottom sheets 702, 704 such that a central opening 706 is provided at a center of the strap 700. As illustrated in FIG. 16D, the top sheet 702 and the outer edges of the top sheet 702 may be slightly more curved and deformed relative to the bottom sheet 704. The downward pressure provided by the pins 624 may press and hold the outer edges of the top sheet 702 to the outer edges of the bottom sheet 704. When the weld points 710 are formed, the top sheet 702 may retain a slight curvature due to the downward pressure provided by the pins 624. The existence or amount of curvature may depend on the width and flexibility of the top and bottom sheets, the depth, geometry and position of the weld points, etc. In some configurations, the welding system 600 may be configured such that the top sheet is not more curved or deformed than the bottom sheet such that both the top and bottom straps are substantially identical.

Figure 17A:
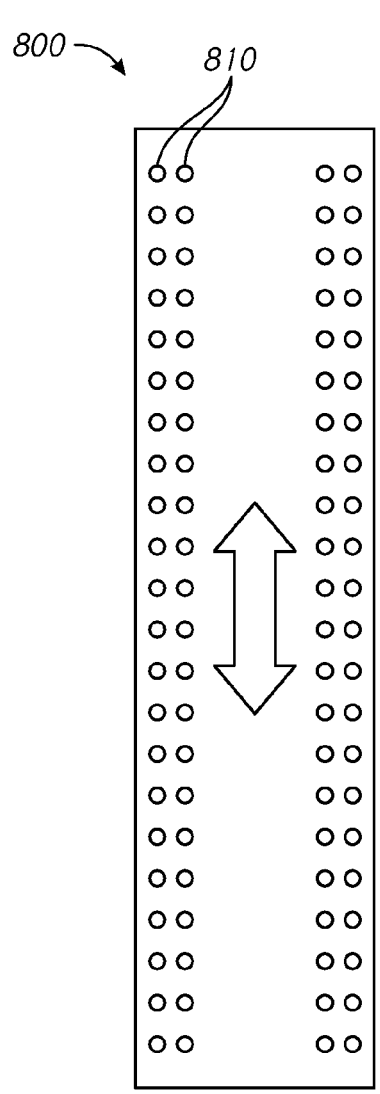
FIGS. 17A and 17B show alternative pin arrangements for the high-frequency welding system.
Figure 17B:
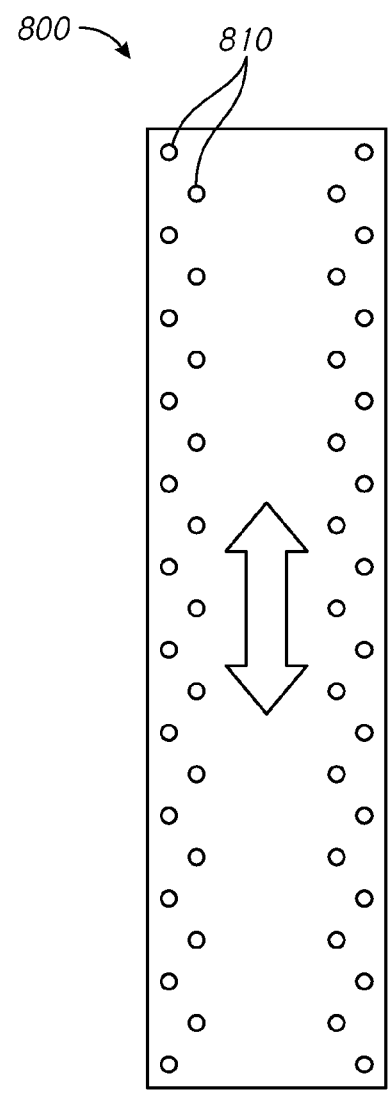

FIGS. 17A and 17B illustrate straps 800 welded together using alternative pin arrangements provided by the welding system 600. FIGS. 17A-B illustrate welded straps 800 having equidistantly spaced weld points 810 that are located along the outer edges of the strap 800. In contrast to the strap 700 in FIGS. 16A-D, the strap 800 in FIG. 17A has double-file rows of linearly spaced weld points 810 along the length of the strap 800. In FIG. 17B, the strap 800 has weld points 810 arranged in a staggered row (i.e., each aperture 810 is offset from an adjacent aperture 810) along the length of the strap 800. The alternative pin arrangements in FIG. 17A-B provide different strength and flexibility characteristics than the single-file pin arrangement of the strap 700 in FIGS. 16A-D. For example, the double-file row of weld points 810 may provide greater weld strength but lower flexibility compared to the single-file row of weld points 710 in FIGS. 16A-D. Conversely, the staggered row of weld points 810 may provide lower weld strength but greater flexibility compared to the single-file row of weld points 710 in FIGS. 16A-D. However, similar to the single-file row of weld points 710 of strap 700, both the double-file and staggered rows of weld points 810 may allow the strap 800 to stretch in a direction parallel to the lengthwise of the strap 800, as indicated by the arrow in FIGS. 17A and 17B. It should be understood that the welding system 600 is not limited to single-file, double-file or staggered pin arrangements and may utilize the pin arrangements disclosed herein according to the desired strength and flexibility characteristics of the strap. Further, although the illustrated embodiments show the top and bottom sheets in a fully overlapping relationship, the top and bottom sheets may still be welded despite only a portion of the top and bottom sheets overlapping.

Certain features, aspects and advantages of some configurations of the present disclosure have been described with reference to high-frequency welding of overlapping headgear straps. However, certain features, aspects and advantages of the methods, apparatus, tools and systems described may be advantageously used on other materials, including but not limited to sheets, plates and films, for the purpose of producing other products, including but not limited to articles of clothing. In addition, certain features, aspects and advantages of the use of methods, apparatus, tools and systems may be equally applied to other welding technologies, including but not limited to ultrasonic welding.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers or components are herein incorporated as if individually set forth.

The disclosed methods, apparatus and systems may also be said broadly to comprise the parts, elements and features referred to or indicated in the disclosure, individually or collectively, in any or all combinations of two or more of said parts, elements or features.

Recitation of ranges herein is merely intended to serve as a shorthand method of referring individually to each separate sub-range or value falling within the range, unless otherwise indicated herein, and each separate sub-range or value is incorporated into the specification as if it were individually recited herein. Moreover, the term "about," when used in combination with a number or a range of numbers, shall be inclusive of standard manufacturing tolerances of the number recited as well as a rounding to the next significant figure represented by the number under standard rounding rules. Moreover, any dimensions or other values provided herein, including the number of decimal places or significant figures provided in such dimensions or values, are merely exemplary, unless otherwise indicated, and include the dimensions or values as rounded to any desired decimal place.

Reference to any prior art in this specification is not, and should not be taken as, an acknowledgement or any form of suggestion that that prior art forms part of the common general knowledge in the field of endeavour in any country in the world.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A method of producing headgear for a patient interface, comprising:
    applying pressure to a weld region defined by overlapping top and bottom headgear straps with a contact surface of a weld tool, wherein the contact surface is separate from a plurality of pins of the weld tool, wherein the plurality of pins conducts electrical or electromagnetic energy, and wherein portions of the contact surface of the weld tool surrounding the pins are inwardly chamfered;
    at least partially penetrating both the top and bottom headgear straps with the plurality of pins; and
    applying high-frequency energy to the weld region through the plurality of pins.

2. The method of claim 1, wherein the plurality of pins fully penetrates the top headgear strap and partially penetrates the bottom headgear strap.

3. The method of claim 2, wherein the plurality of pins penetrates about 20% of the depth of the bottom headgear strap.

4. The method of claim 1, wherein the contact surface of the weld tool that faces the weld region comprises beveled or rounded edges.

5. The method of claim 1, wherein the chamfered portions are substantially arcuate.

6. The method of claim 5, wherein the substantially arcuate chamfered portions are defined by crater-shaped recesses present in the contact surface of the weld tool.

7. The method of claim 6, wherein the curvatures of the sides of the crater-shaped recesses are defined by substantially circular cross-sections of the weld tool having radii x that are proportional to the average distance between each of the plurality of pins y according to the ratio x:y=about 0.3 to about 0.4.

8. The method of claim 1, wherein the plurality of pins is arranged in a plurality of rows.

9. The method of claim 8, wherein the rows are offset such that the plurality of pins is present in a honeycomb arrangement.

10. The method of claim 1, wherein the plurality of pins is arranged such that each pin is substantially equidistant from adjacent pins.

11. The method of claim 1, wherein either the top or bottom headgear straps comprises an edge section and a body section, the edge section having a smaller width than the body section.

12. The method of claim 11, wherein the width of the edge section is in the range of about 80% to about 90% of the width of the body section.

13. The method of claim 11, wherein a substantially curved transition region lies between the body section and the edge section.

14. The method of claim 1, wherein the average distance between adjacent pins of the plurality of pins is in the range of about 1.5 mm to about 2.0 mm.

15. The method of claim 1, wherein the average distance between adjacent pins of the plurality of pins is in the range of about 3 to about 4 times the average width of the pins.

16. The method of claim 1, wherein each of the plurality of pins has an exposed pin head at one end of the weld tool and a protruding pin tip opposite the pin head.

17. The method of claim 1, wherein the inwardly chamfered surfaces define a discrete cavity for each pin.

18. The method of claim 1, wherein each of the plurality of pins has a pointed tip that pierces an outer surface of the top headgear strap.

19. The method of claim 18, wherein each of the plurality of pins penetrates entirely through the top headgear strap and at least partially through the bottom headgear strap.

* * * * *